US008428730B2

(12) United States Patent
Stack et al.

(10) Patent No.: US 8,428,730 B2
(45) Date of Patent: Apr. 23, 2013

(54) TRANSVASCULAR ELECTRODE SYSTEM AND METHOD

(75) Inventors: Richard S. Stack, Chapel Hill, NC (US); Michael S. Williams, Santa Rosa, CA (US); Daniel W. Fifer, Windsor, CA (US); Richard A. Glenn, Santa Rosa, CA (US); Geoffrey A. Orth, Sebastopol, CA (US); Lynn Elliott, Maple Grove, MN (US); Colleen Stack N'diaye, Durham, CA (US)

(73) Assignee: Synecor LLC, Chapel Hill, NC (US)

( * ) Notice: Subject to any disclaimer, the term of this patent is extended or adjusted under 35 U.S.C. 154(b) by 0 days.

(21) Appl. No.: 13/286,217

(22) Filed: Nov. 1, 2011

(65) Prior Publication Data

US 2012/0221014 A1 Aug. 30, 2012

Related U.S. Application Data

(63) Continuation of application No. 13/042,350, filed on Mar. 7, 2011, which is a continuation of application No. 12/413,495, filed on Mar. 27, 2009, now Pat. No. 7,925,352.

(60) Provisional application No. 61/039,793, filed on Mar. 27, 2008.

(51) Int. Cl.
*A61N 1/00* (2006.01)

(52) U.S. Cl.
USPC ............................................................ 607/44

(58) Field of Classification Search ............. 607/44; 606/41, 129
See application file for complete search history.

(56) References Cited

U.S. PATENT DOCUMENTS 6,315,778 B1 * 11/2001 Gambale et al. ............... 606/41
2011/0152877 A1 * 6/2011 Bly ............................... 606/129

* cited by examiner

*Primary Examiner* — George Manuel
*Assistant Examiner* — Robert N Wieland

(57) ABSTRACT

A transvascular electrode system includes an expandable electrode-carrying anchor. The anchor is intravascularly advanced in a compressed position to a first site in a blood vessel. A first portion of the anchor expands to position an electrode against the vessel wall, while a second portion remains is compressed. Mapping is performed by delivering stimulation energy from the electrode and measuring the response (e.g. blood pressure, heart rate, and/or related parameters). The first portion is at least partially collapsed and the electrode system is moved to a second site. The first portion is expanded to position the electrode into against the vessel wall, while the second portion remains compressed. Additional mapping is performed. The process is repeated until the anchor electrode position is optimized, at which point the second portion of the anchor is expanded to chronically retain the electrode in the vessel.

9 Claims, 18 Drawing Sheets

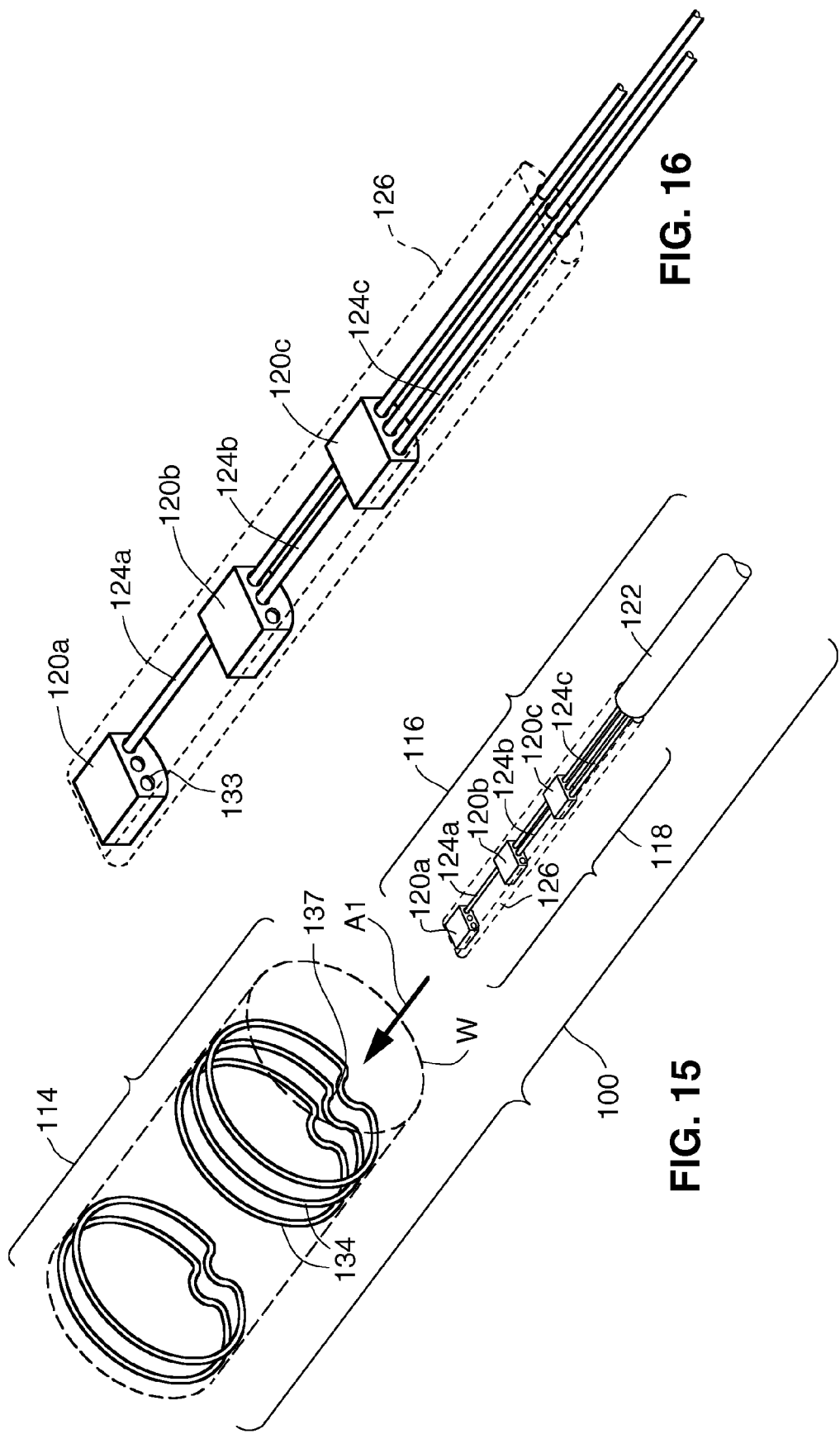

TRANSVASCULAR ELECTRODE SYSTEM AND METHOD

RELATED APPLICATIONS

This application is a continuation of U.S. Ser. No. 13/042,350, filed Mar. 7, 2011, which is a continuation of U.S. Ser. No. 12/413,495, filed Mar. 27, 2009, now U.S. Pat. No. 7,925,352, which claims the benefit of U.S. Provisional Application No. 61/039,793, filed Mar. 27, 2008. Each of the forgoing applications is incorporated herein by reference.

FIELD OF THE INVENTION

The present invention generally relates to implantable devices and systems, and associated methods for delivering therapy to nerve structures using components implanted within the vasculature.

BACKGROUND OF THE INVENTION

Heart failure (HF) is a condition characterized by reduced cardiac output that triggers neurohormonal activation. This compensatory mechanism functions acutely to increase cardiac output and restore left ventricular (LV) functional capacity such that patients remain asymptomatic. Over time, however, sustained activation of these neurohormonal systems triggers pathologic LV remodeling and end-organ damage that ultimately drives the progression of HF.

In many people, persistent hypertension is the predominant contributing factor for development of HF. Management of hypertension can slow or prevent the natural evolution of HF.

The human body maintains blood pressure through the use of a central control mechanism located in the brain with numerous peripheral blood pressure sensing components. These components are generally made of specialized cells embedded in the walls of blood vessels that create action potentials at an increased rate as the cell is stretched. These groups of cells are generally referred to as baroreceptors. The action potentials are propagated back to the central control center via neural pathways along afferent nerves. While there are many baroreceptor components located throughout the body, there are several that are particularly important. Possibly the most important baroreceptor region is located near the bifurcation of the common carotid artery into the internal and external carotid. In this area there is a small enlargement of the vessel tissues, referred to as the carotid bulb or carotid sinus. The carotid baroreceptors are generally found throughout this area. The carotid baroreceptors and related neural pathways form the primary pressure sensing component that provides signals to the brain for regulating cranial and systemic blood pressure.

Applicant's prior Application Publication No. U.S. 2007/0255379, which is incorporated herein by reference, discloses an intravascular neurostimulation device (such as a pulse generator) and associated methods for using the neurostimulation device to stimulate nervous system targets. As discussed in that application, targeting stimulation to baroreceptor afferents in HF patients can lead to decreases in sympathetic tone, peripheral vascular resistance, and afterload. Such stimulation can be used to control blood pressure as a treatment for hypertension or HF. Stimulation of the vagus nerve (e.g. vagal efferents) is known to cause a reduction in heart rate.

The present disclosure describes an implementation of Applicants' previously-disclosed intravascular systems and methods for use in stimulating nervous system targets such as the vagus nerve and/or its branches, the carotid artery, the carotid sinus nerve and/or its branches, baroreceptors, and/or for otherwise activating a baroreceptor response. Systems and methods of the type disclosed may be used for controlling heart rate and/or regulating blood pressure for treatment of hypertension, congestive heart failure or other conditions.

The internal jugular vein, vagus nerve, and common carotid artery (which includes the carotid sinus) are located within the carotid sheath, a fascial compartment within the neck. The carotid sheath provides relatively fixed geometric relationships between these structures while also giving some degree of insulation from surrounding tissue. According to one embodiment disclosed herein, a method is disclosed for transvascularly stimulating contents of the carotid sheath. The method includes advancing an energy delivery element, which may be an electrode, into an internal jugular vein, retaining the energy delivery element in a portion of the internal jugular vein contained within a carotid sheath, and energizing the energy delivery element to transvenously direct energy to target contents of the carotid sheath external to the internal jugular vein. The energy may be directed to a carotid artery within the carotid sinus sheath, and/or to a carotid sinus nerve or nerve branch within the carotid sinus sheath, to nerve branches emanating from carotid artery baroreceptors, and/or to a vagus nerve or nerve branch within the carotid sinus sheath.

In some of the disclosed embodiments, a second electrode or other second energy delivery element is introduced into a second internal jugular vein and retained in a portion of the second internal jugular vein contained within a second carotid sheath. The second energy delivery element is energized to direct energy to contents of the second carotid sheath external to the second internal jugular vein.

Shielding may be used to minimize collateral stimulation of unintended targets. In one embodiment, a shield is positioned at least partially surrounding the carotid sinus sheath. The shield blocks conduction of energy beyond the sheath during energization of the energy delivery element. In another embodiment, an insulative material is delivered into extravascular space adjacent to the internal jugular vein. The insulative material defines a channel within the extravascular space. Energizing the energy delivery implant causes energy to conduct along the channel to the target contents of the sheath.

In some embodiments, the system may include a plurality of electrodes disposed on the lead, the electrodes including a first array and a second array, wherein the first and second arrays are positioned such that when the first array is positioned in the internal jugular vein to direct stimulation energy transvascularly to a vagus nerve in the carotid sheath, the second array is positioned to direct stimulation energy transvascularly towards a carotid artery or carotid sinus nerve/nerve branch within the carotid sheath. In other embodiments, the same array of electrodes delivers stimulus to each of the target structures within the carotid sheath.

The baroreceptors in the aorta are the second best understood baroreceptors and are also a powerful localized blood pressure sensing component. The aortic baroreceptors are also responsible for providing signals to the brain for regulating systemic/peripheral blood pressure. Some of the embodiments disclosed herein are positioned to transvascularly deliver energy to these baroreceptors and/or associated nerve structures as an alternative means for neurohormonal control.

BRIEF DESCRIPTION OF THE DRAWINGS

FIG. 2A is a schematic cross-section view of the sheath. FIG. 2B is a side view showing contents of the sheath, with the sheath removed.

In FIG. 5B, the pulmonary artery is shown in cross-section taken along the plane indicated by arrows 5B-5B in FIG. 5A.

FIG. 15 is a perspective view showing an anchor and lead system, with the lead fully detached from the anchor. The anchor is schematically shown disposed within a portion of a blood vessel, the walls of which are shown as transparent.

FIG. 16 is a perspective view of the lead of FIG. 15, with the cable removed from the conductors. The member is shown transparent.

DETAILED DESCRIPTION

Figure 1A:
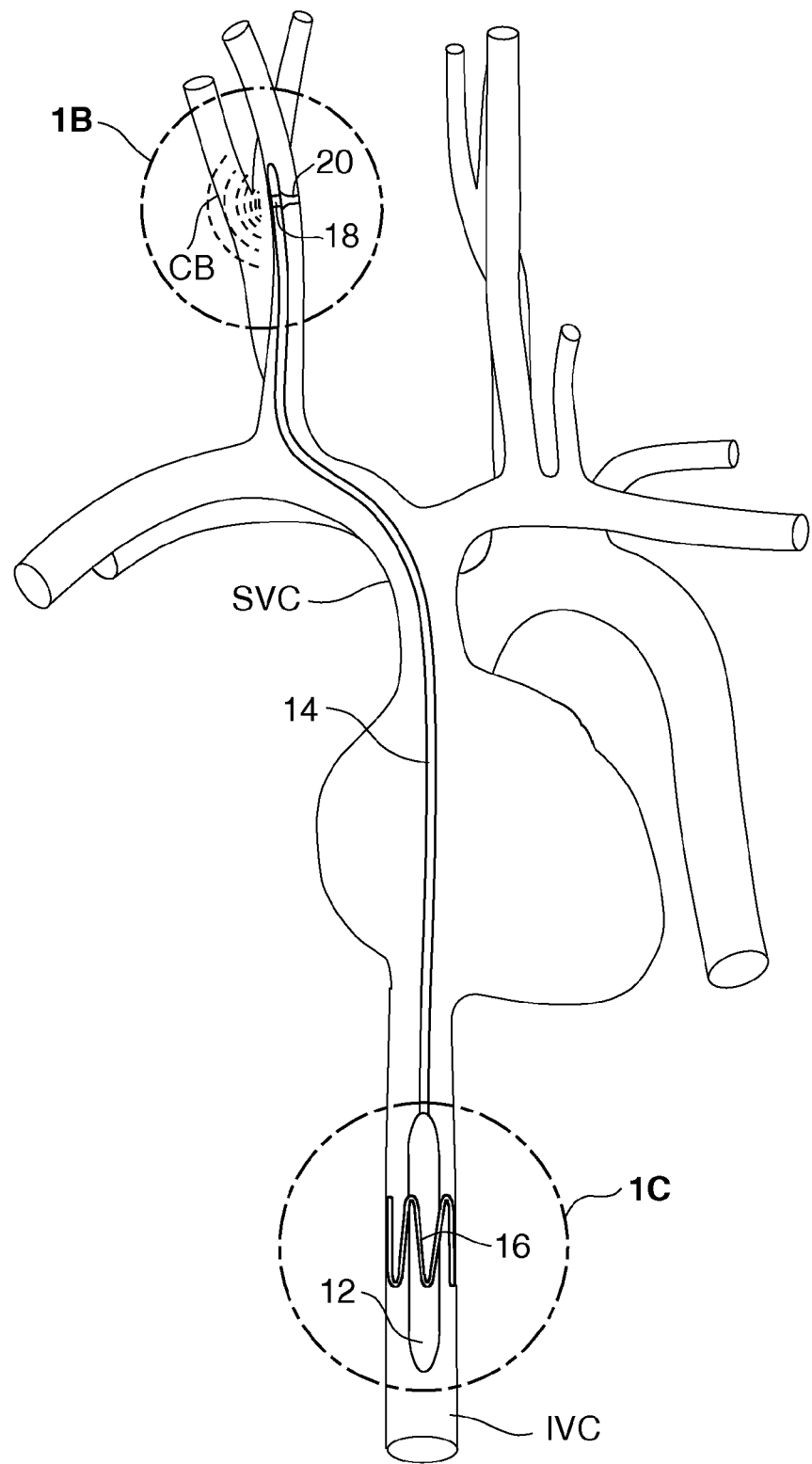
FIG. 1A schematically illustrates intravascular positioning of an intravascular neurostimulation system for stimulation of the carotid sinus bulb.

Referring to FIG. 1A, in a first embodiment, system 10 includes a housing 12 containing the necessary pulse generator and associated electronics, circuitry and related components and at least one lead 14 carrying some or all of the electrodes 18 needed to deliver electrical energy to nervous system structures. In the illustrated embodiment, the housing 12 is positioned in the inferior vena cava ("IVC"), but it may alternatively be positioned in other vessels including, but not limited to, the superior vena cava ("SVC") (see FIG. 6, for example), or the left or right subclavian vein ("LSV" or "RSV"). An anchor 16 is used to retain the housing within the vasculature. Features suitable for use with the system, including embodiments of leads, electrodes, housings and anchors are shown and described in the following patents and applications, each of which is incorporated herein by reference: U.S. Pat. No. 7,082,336 entitled IMPLANTABLE INTRAVASCULAR DEVICE FOR DEFIBRILLATION AND/OR PACING, U.S. 2005-0043765 entitled INTRAVASCULAR ELECTROPHYSIOLOGICAL SYSTEM AND METHODS, U.S. US 2005-0228471, entitled METHOD AND APPARATUS FOR RETAINING MEDICAL IMPLANTS WITHIN BODY VESSELS, U.S. Pat. No. 7,363,082, entitled FLEXIBLE HERMETIC ENCLOSURE FOR IMPLANTABLE MEDICAL DEVICES, U.S. US 2005-0154437, entitled IMPLANTABLE MEDICAL DEVICE HAVING PRE-IMPLANT EXOSKELETON, and U.S. 2007/0255379, entitled INTRAVASCULAR DEVICE FOR NEUROMODULATION. Each of these prior patents/applications is incorporated herein by reference.

Figure 1B:
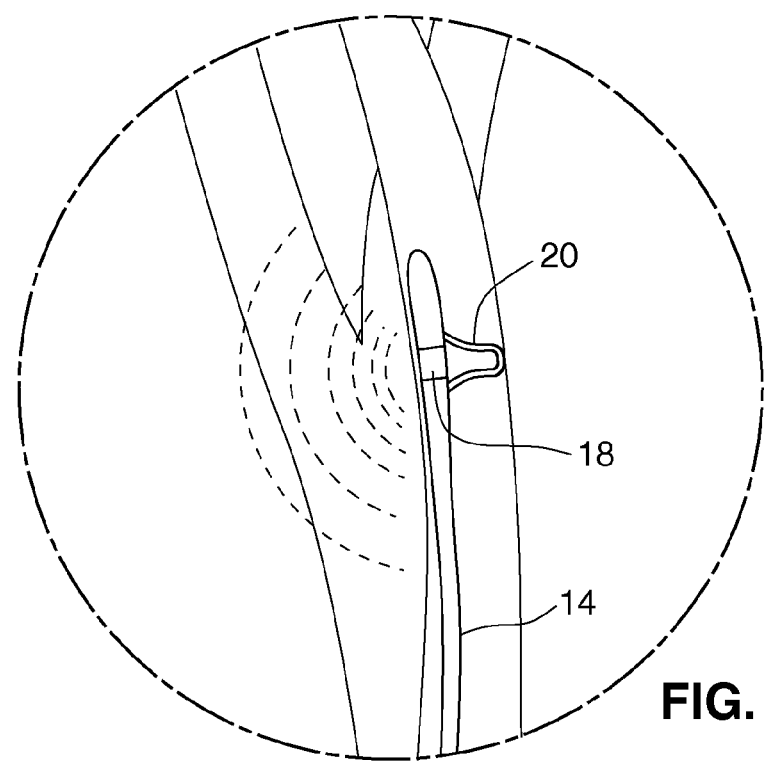
FIG. 1B is a detail view of the area identified by circle 1B-1B in FIG. 1A showing the lead anchored in the internal jugular vein.
Figure 1C:
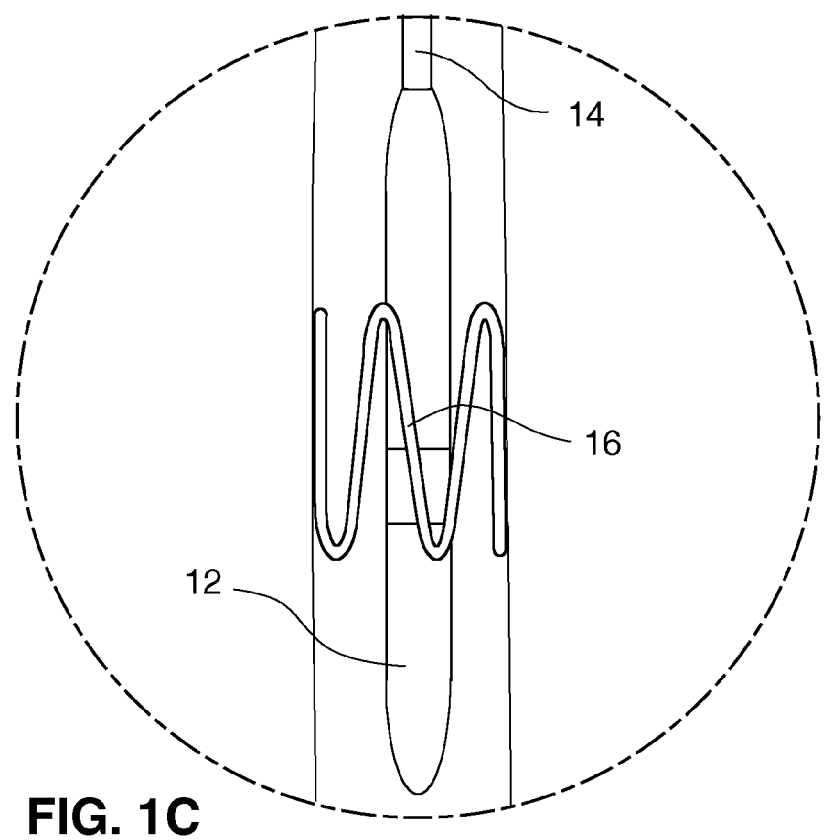
FIG. 1C illustrates anchoring of the housing in the inferior vena cava.

The lead 14 is intravascularly positioned such that electrodes are oriented to stimulate nervous system structures outside the vessel within which the electrodes are placed. In the embodiment shown in FIGS. 1A and 1B, the electrodes are placed in the venous system and oriented towards the carotid bulb CB to allow electrical energy from the electrodes to be targeted towards the baroreceptors of the carotid artery and/or the carotid sinus nerves or associated nerves or nerve branches. In this embodiment, lead 14 is delivered via the internal jugular vein (Ii) to the location in the neck at the common carotid bifurcation. As best shown in FIG. 1B, an anchor 20 coupled to the lead 14 may expand into contact with the walls of the internal jugular vein to maintain the position of the electrodes. From this electrode location, neurostimulation therapy can be delivered transvascularly from electrodes on the lead or anchor towards the carotid bulb. Stimulation of the baroreceptors of the carotid bulb, or the associated carotid sinus nerves and/or nerve branches, activates a baro-response which controls blood pressure for the treatment of hypertension and/or heart failure.

Figure 1D:
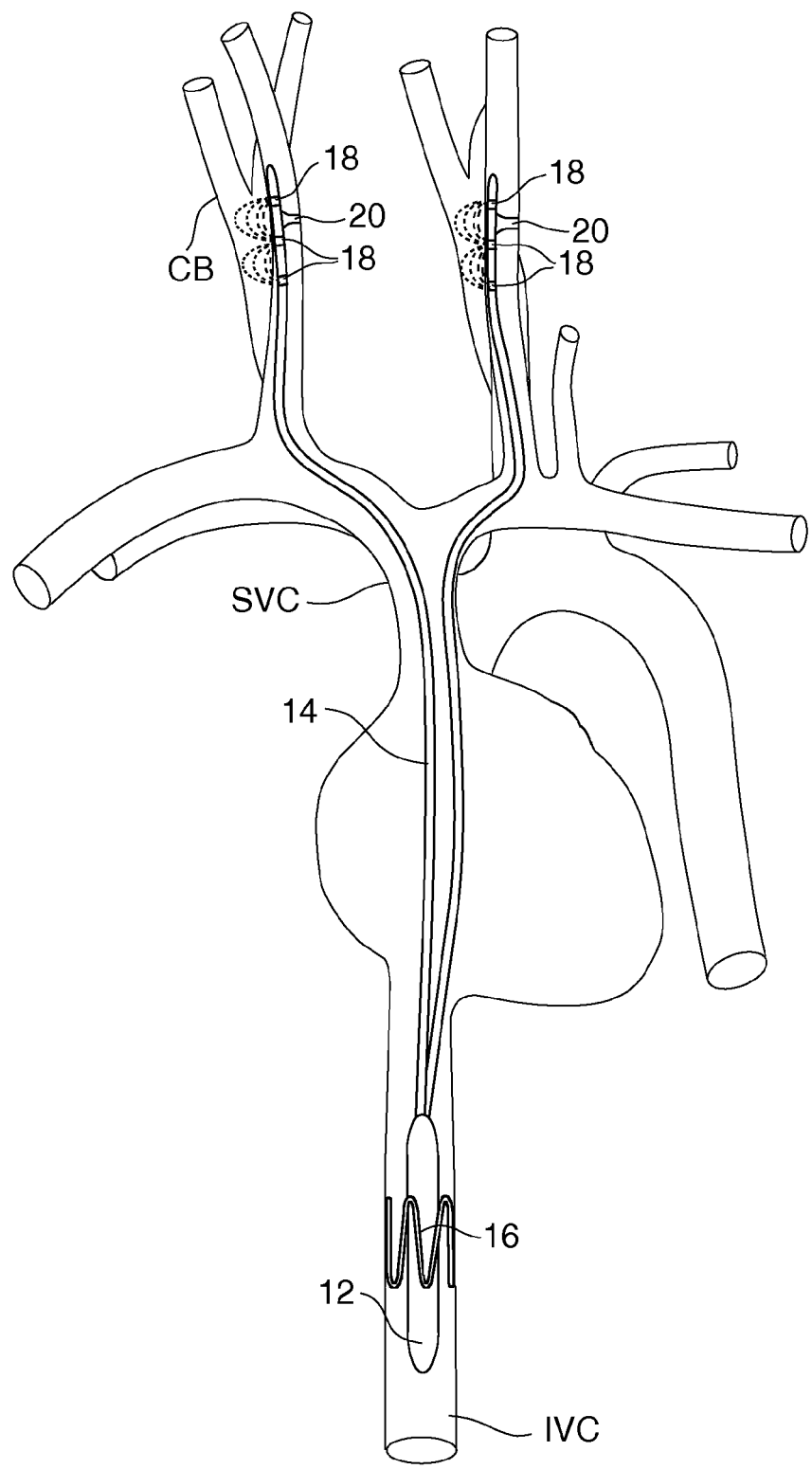
FIG. 1D is similar to FIG. 1A but shows a bi-lateral arrangement of stimulation leads.

Referring to FIG. 1D, the FIG. 1A embodiment may be adapted for bi-lateral stimulation as also discussed below in connection with FIG. 3. More specifically, electrodes 18 may be anchored in both the left and right internal jugular veins for simulation of the carotid sinus bulbs on both the left and right side of the vasculature. The FIG. 1D embodiment illustrates a tripolar arrangement of electrodes.

In some embodiments, electrodes are intravascularly positioned to stimulate multiple neurological targets. For example, electrodes positioned in the internal jugular for stimulation of carotid sinus nerve targets (e.g. the carotid sinus nerves or associated baroreceptors) may also be used to additionally stimulate the vagus nerve.

Figure 2A:
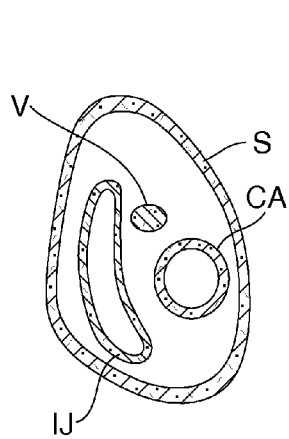
FIGS. 2A and 2B schematically illustrate the arrangement of the internal jugular vein, carotid artery, and vagus nerve within the carotid sheath.
Figure 2B:
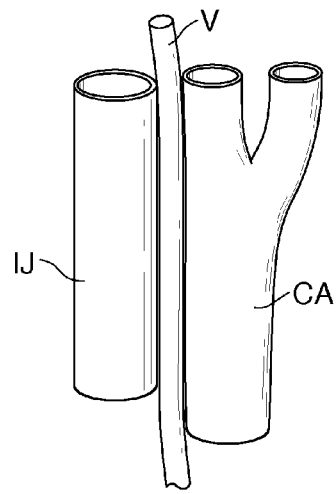

As illustrated in FIGS. 2A and 2B, the internal jugular IJ, vagus nerve V, and common carotid artery CA (which includes the carotid sinus) are located within the carotid sheath S, a fascial compartment within the neck. Sheath S provides relatively fixed geometric relationships between these structures while also giving some degree of insulation from other surrounding tissue. The embodiments of FIGS. 3A-3C take advantage of these geometric relationships in utilizing a single neurostimulation delivery device for directing electrical energy towards both the vagus nerve and the carotid bulb. According to one such embodiment, a single lead is delivered to position electrode(s) in the portion of internal jugular vein disposed within the sheath S, i.e. near the site of the right carotid bifurcation as discussed in connection with FIG. 1A-1B. Positioning of the electrode within the carotid sheath may be confirmed using angiography or carotid ultrasound.

The system operates to stimulate both the vagus nerve and carotid sinus nerve targets using electrodes on the IJ lead. Stimulation of each such structure may be achieved using the same set of electrodes 18a (FIG. 3B) utilizing the same electrical stimulation protocol, while simultaneously preventing the stimulation of other structures in the neck.

Stimulating the contents of the carotid sheath S can counteract compensatory mechanisms that drive disease progression in chronic HF. Specifically, such stimulation may be used to reduce sympathetic activation and enhance sympathetic tone, and to improve hemodynamics (peripheral vascular resistance, afterload, cycle length and stroke volume) to reduce blood pressure and heart rate.

The electrodes 18a may be positioned to extend both longitudinally (FIG. 3A) and circumferentially (FIG. 3B) along a portion of the internal jugular, or in any arrangement that will generate stimulation patterns oriented to capture both the vagus nerve and carotid sinus nerve targets (e.g. the carotid sinus nerves, nerve branches, and/or associated baroreceptors).

Therapeutic activation of these structures will provide multiple benefits, including 1) activation of the baro-response to lower blood pressure, 2) activation of the parasympathetic afferent and efferent pathways to help rebalance the sympathetic/parasympathetic imbalance that is common in heart failure patients, 3) mild reduction in heart rate (through vagal stimulation) that can reduce total cardiac energy consumption, reduce diastolic pressures, reduce mean arterial pressures, and possibly reduce afterload.

Figure 3A:
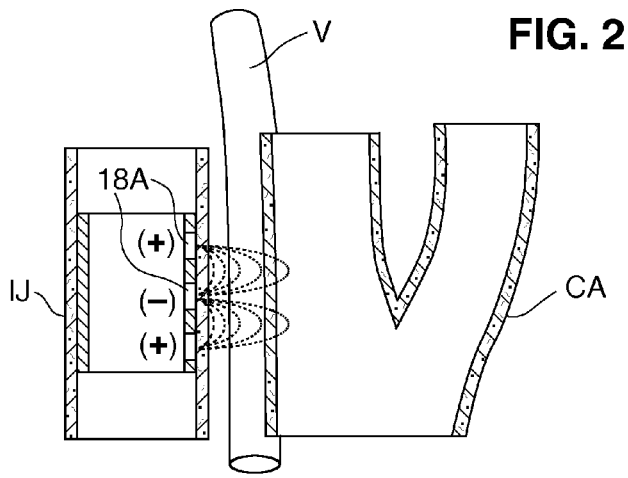
FIG. 3A is a schematic representation of an internal jugular vein, carotid bulb and vagus nerve and illustrates a first electrode arrangement for stimulating the contents of the carotid sheath, such as the carotid artery and vagus nerve.
Figure 3B:
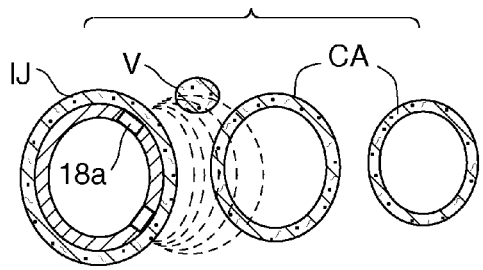
FIG. 3B schematically illustrates, in cross-section, an internal jugular vein, vagus nerve, and carotid sinus, and schematically shows a second electrode arrangement for stimulating the carotid bulb and vagus nerve.
Figure 3C:
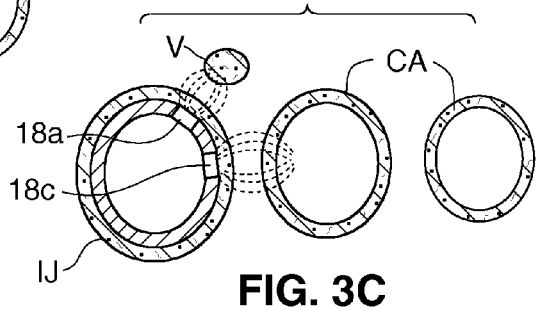
FIG. 3C is similar to FIG. 3B and schematically shows a third electrode arrangement for stimulating the carotid bulb and vagus nerve.

In a modification to the FIG. 3B embodiment, dedicated electrodes are positioned for each type of target as shown in FIG. 3C, in which electrodes 18b are positioned to stimulate the vagus nerve while electrodes 18c are positioned to stimulate the carotid sinus.

Figure 4A:
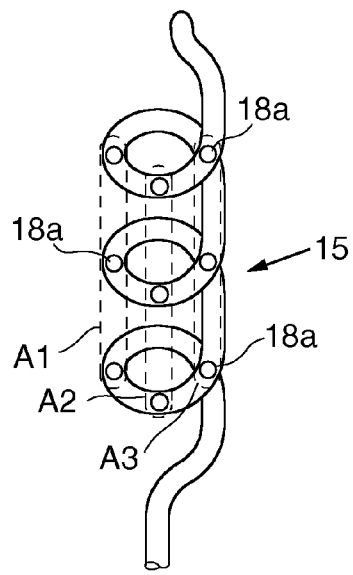
FIG. 4A is a perspective view of a distal portion of an intravascular stimulation lead including a first electrode design which may be used to direct simulation energy towards contents of the carotid sheath.
Figure 4B:
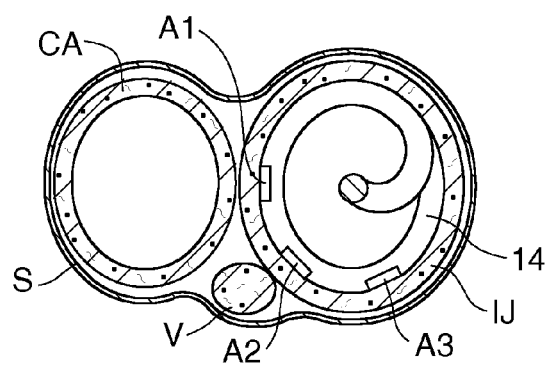
FIG. 4B is a cross-section view of the carotid sheath showing the lead of FIG. 4A positioned in the internal jugular vein.

In one exemplary arrangement shown in FIGS. 4A and 4B, the lead 14 has a spiral-shaped section 15 which may be on the distal section of the lead. Electrodes 18a are positioned on the spiral 15 such that electrodes line up in multiple circumferentially spaced longitudinal arrays, such as arrays A1, A2 and A2 as shown. As can be seen in the cross-section view of FIG. 4B, when the lead is implanted a first one of the arrays A1 is positioned to direct stimulation energy towards the carotid artery or associated carotid sinus nerve targets, and a second one of the arrays A2 is positioned to direct stimulation energy towards the vagus nerve. Determination of which of the arrays is located for the most optimal stimulation of which structure may be determined during implantation by measuring blood pressure and heart rate feedback, or related parameters. This allows the user to program the stimulation device to energize the electrodes in array A1 in accordance with a stimulation algorithm best suited for stimulation of the carotid artery or carotid sinus nerve targets, and to energize the electrodes in array A2 in accordance with a stimulation algorithm best suited for vagal nerve stimulation.

In an alternative embodiment, the arrays of electrodes may be positioned on an expandable stent-like anchor of the type described below in connection with FIG. 9A, for example. See also FIGS. 3A-3C. The anchor might take the form of a self-expandable mesh formed of a polymeric material or other insulated material. With this form of anchor, the anchor can be provided with insulation around a majority of its circumference, allowing stimulation energy to be directed only towards the target structures, thereby minimizing collateral stimulation. It should be noted that while "stent-like" anchors resemble stents in the sense that they are expandable so as to radially engage a vascular wall, the anchors need not have the hoop strength possessed by conventional stents as needed by such stents to maintain patency of the diseased vessels within which they are conventionally implanted.

Figure 4C:
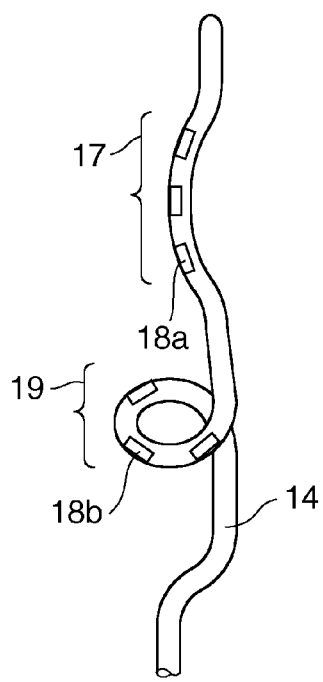
FIG. 4C is a perspective view similar to FIG. 4A showing the distal portion of an alternative lead having electrodes suitable for directing simulation energy towards contents of the carotid sheath.
Figure 4D:
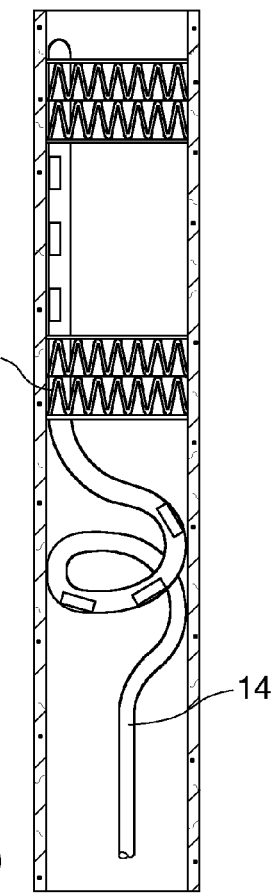
FIG. 4D is a side elevation view showing the lead of FIG. 5A anchored in a blood vessel.

In another alternative shown in FIGS. 4C and 4D, the lead 14 includes a first, longitudinal, section 17 including a first electrode array having electrodes 18a positioned to direct energy towards the carotid artery and/or carotid sinus nerve or associated nerve structures. The longitudinal section 17 may be pre-shaped to include a laterally extending curve having a spring force that will bias the associated electrodes 18a on the longitudinal section 17 in apposition with the vessel wall. A second section 19 has a second electrode array having electrodes 18b positioned to direct energy towards the vagus nerve. The second section 19 may be partially circumferential as shown, so that the electrodes 18b are spaced generally circumferentially to optimize capture of the vagus nerve. One or more anchors 16 may be used to support the lead as shown.

Further alternatives to the FIG. 3A-3C embodiment include delivering a lead to both the right and left side of the neck for bilateral stimulation of the carotid bulbs while only stimulating the right side vagus nerve, 2) delivering a lead to both the right and left side of the neck for bilateral stimulation of the carotid bulbs and bilateral stimulation of the vagus nerve (see e.g. FIG. 1D), 3) utilizing any of the previously described lead configurations but utilizing separate energy delivery protocols for stimulating the carotid baro-response and vagal nerve. Implementations of this latter concept might include (a) interleaving/multiplexing (time sequencing where an "a" therapy is on for a pre-determined or adaptively determined duration followed by a "b" therapy that is on for a predetermined or adaptively determined time in a repeating "a"/"b" sequence) the delivery of two separate electrical stimulation protocols utilizing the same stimulation electrodes or (b) having a multiplicity of electrodes on the lead such that one set of electrodes can be utilized to uniquely stimulate the carotid baro-response and a second set of electrodes can be utilized to uniquely stimulate the vagus nerve (e.g. as in the FIG. 4A-4C embodiments), these therapies would be independent of each other so could be delivered simultaneously but could also be sequenced as described in (a).

In another embodiment, electrodes anchored in the pulmonary artery may be used to simulate neurological targets associated with baroreceptors of the aortic arch. Such targets can include the baroreceptors themselves or the associated nerves. As discussed in the Background section, the aortic baroreceptors are a powerful localized blood pressure sensing component and are also responsible for providing signals to the brain for regulating systemic/peripheral blood pressure. The present embodiment takes advantage of the positional relationship between the aortic arch and the pulmonary artery to position electrodes for stimulation of the aortic baroreceptors. In the human anatomy, the aortic arch crosses the pulmonary artery above the pulmonary artery bifurcation. At this point the pulmonary artery and the aortic artery are in intimate contact. The aortic baroreceptors are co-located at this point. All of these structures are co-located within the thoracic cavity and remain in a relatively fixed geometric relationship. The following embodiment utilizes a single neurostimulation delivery device for stimulating the aortic arch and activating a baro response for blood pressure control in the treatment of hypertension or congestive heart failure.

Figure 5A:
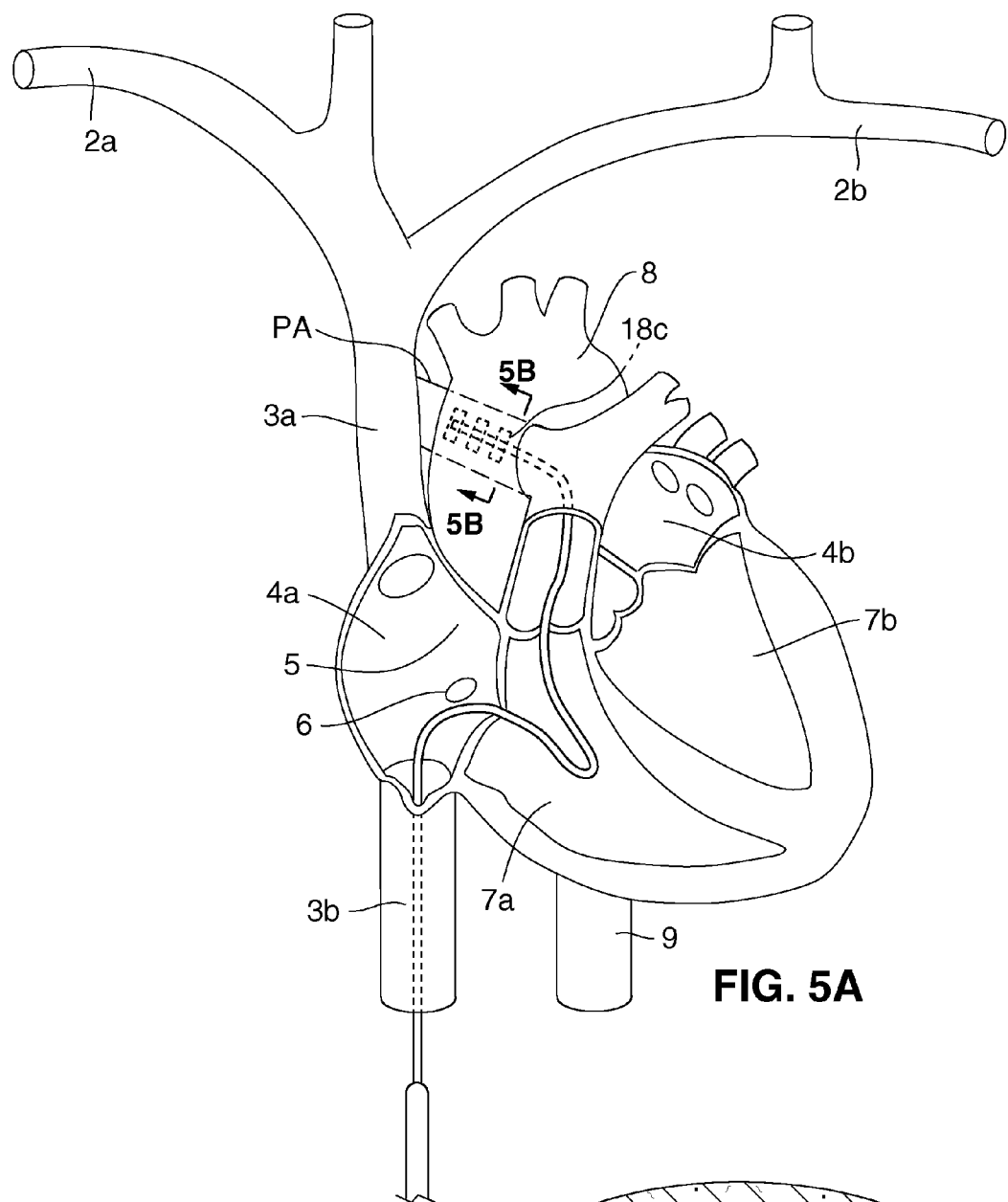
FIGS. 5A and 5B schematically illustrate positioning of a system with electrodes in the pulmonary artery for aortic arch baroreceptor stimulation.
Figure 5B:
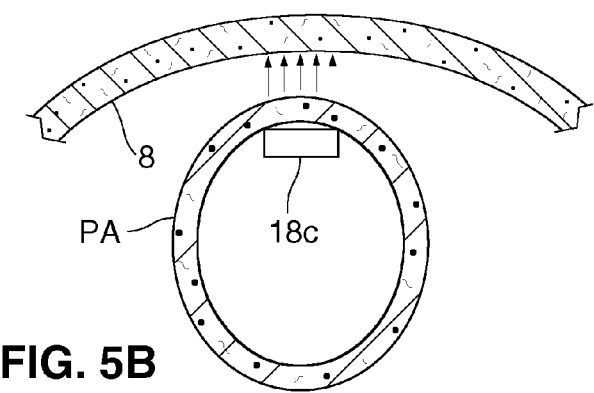

In a preferred configuration for implementing this embodiment, a single intravascular lead is delivered to the site of the pulmonary artery/aortic arch intersection point. The lead is anchored in the pulmonary artery at this location so as to position the electrodes for optimal stimulation of the aortic arch baroreceptors, while simultaneously preventing the stimulation of other structures in the chest cavity. FIGS. 5A and 5B illustrate that by positioning the electrodes 18c at or near the portion of the pulmonary artery PA, crossing over the aortic arch 8, the electrical field can be directed towards the aortic arch. Access to the pulmonary artery can be gained by extending the electrode leads through the IVC or SVC to the right atrium, then into the right ventricle and out of the heart into the pulmonary artery. See FIG. 5A. The device would be capable of all the stimulation protocols, isolation/insulation, utilization of sensors, external communication and programming, energy/power sources, implant tools and techniques as used for the jugular based system, including those disclosed herein and in Applicant's prior Application Publication No. U.S. 2007/0255379.

Alternatives to the FIG. 5A embodiment include other venous routes for transvenous stimulation of the aortic arch baroreceptors. For example an intravascular lead could be positioned in the left innominate vein. Other baroreceptors besides those clustered in the aortic arch may be stimulated with this device. For example, electrodes could be positioned within the pulmonary artery (main, left, right, or any combination of these) in order to stimulate pulmonary artery baroreceptors. This may be performed in isolation or in combination with stimulation directed toward the baroreceptors of the aortic arch. This is one example of many possible target combinations that could be utilized in transvascular baroreceptor stimulation from within the great vessels The embodiment of FIGS. 5A-5B may be further modified to include vagus nerve stimulation in additional to stimulation of baroreceptors of the aortic arch (or associated nerves). Examples of electrode placement according to this embodiment are illustrated in FIGS. 7A through 7C, each of which represents the region of the heart and neighboring vasculature defined by the region marked by circle 7-7 in FIG. 6. In these figures, anchors for the portion of the lead carrying the electrodes are not shown for clarity.

Figure 6:
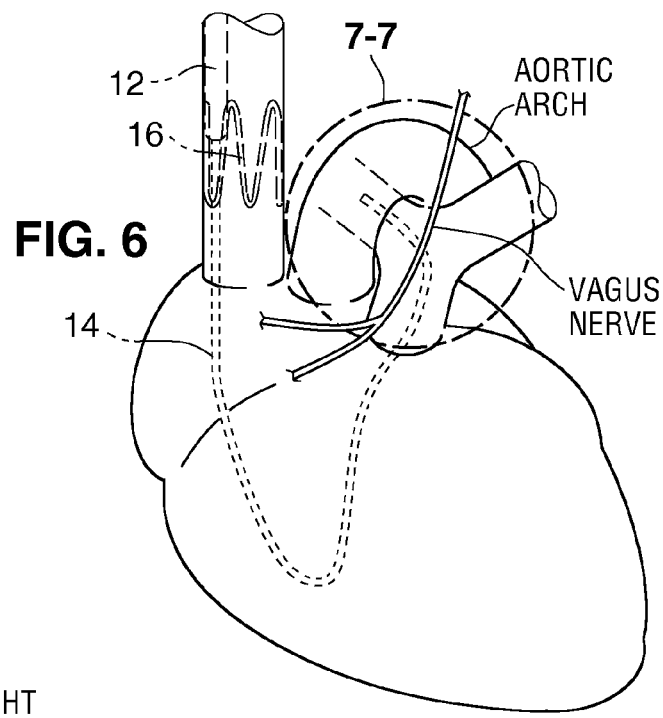
FIG. 6 schematically illustrates positioning of a system with a lead positioned to place electrodes for stimulation of aortic arch baroreceptors and the vagus nerve.
Figure 7A:
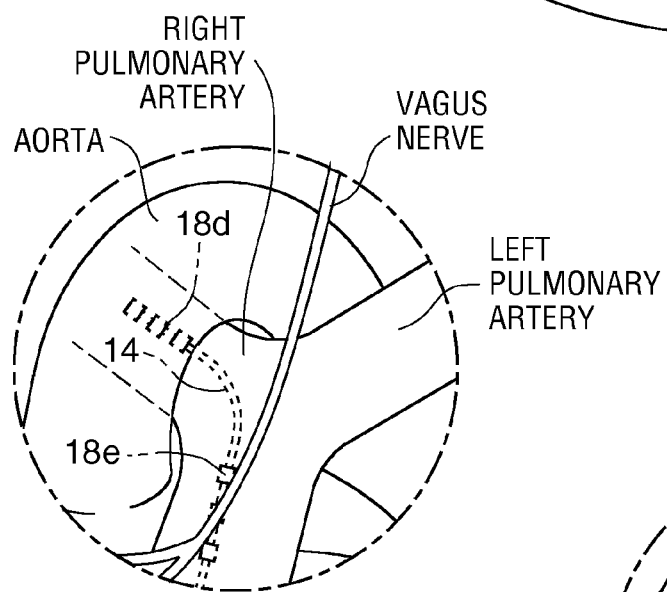
FIG. 7A schematically illustrates the region identified by circle 7-7 in FIG. 6 and illustrates a first embodiment of electrode positions for the lead.
Figure 7B:
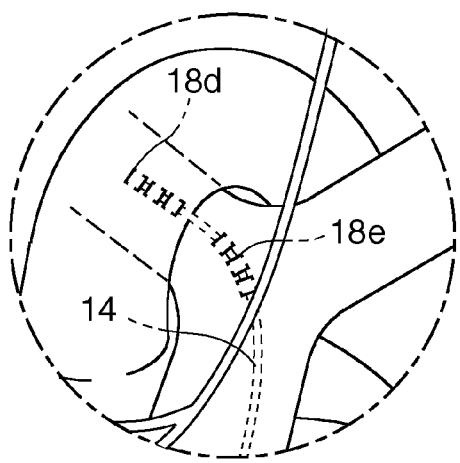
FIGS. 7B through 7D are similar to FIG. 7A and show alternate embodiments of electrode positions for the lead.
Figure 7C:
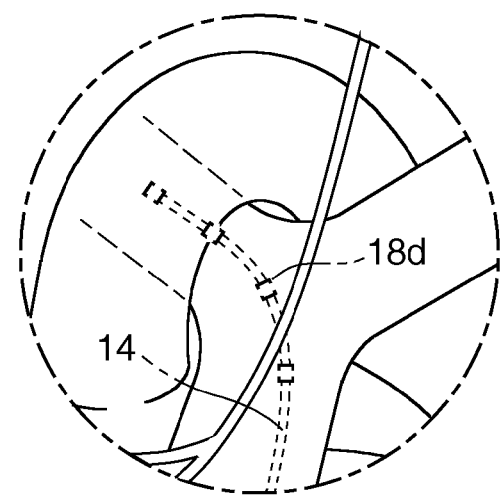

Referring to FIG. 6, in the human anatomy the aortic arch crosses the pulmonary artery above the pulmonary artery bifurcation; at this point the pulmonary artery and the aortic artery are in intimate contact. The aortic baroreceptors are also at this location. A branch of the vagus nerve follows the crease at the base of the heart (more or less the division between the upper and lower chambers of the heart). Efferent fibers innervate the right atria and are involved in the control of heart rate. Afferent fibers continue to the location of the aortic arch baroreceptors and conduct signals back to the brain for control of systemic blood pressure. The current embodiment utilizes a single neurostimulation delivery device for activating both the vagus nerve and the baroreceptors of the aortic arch.

Referring to FIG. 7A, in a first embodiment, a single intravascular lead 14 is delivered to the site of the pulmonary artery/aortic arch intersection point. The lead 14 is anchored in the pulmonary artery at this location in such a way as to position the electrodes 18d for optimal stimulation of the aortic arch baroreceptors, and to position the electrodes 18d in the early pulmonary artery for stimulation of the vagus nerve. This arrangement allows simulation of the vagus nerve and aortic arch baroreceptors from the same lead, potentially utilizing the same electrical stimulation protocol, while simultaneously preventing the stimulation of other structures in the chest cavity. In an alternative to this arrangement, separate leads may be used to position the electrodes 18d and the electrodes 18e. For example, one method might include delivering one lead to the pulmonary artery at the intersection with the aortic arch, such that stimulation electrodes 18d are optimally positioned and anchored to stimulate the aortic arch baroreceptors, and delivering a second lead having electrodes 18e to the outflow track of the pulmonary, such that electrodes 18e are positioned and anchored to optimally stimulate the vagus nerve.

In an alternate embodiment shown in FIG. 7B, lead 14 is delivered to the pulmonary artery at the intersection with the aortic arch. Stimulation electrodes 18d are optimally positioned and anchored to stimulate the aortic arch baroreceptors. This embodiment differs from the FIG. 7A embodiment in that here electrodes 18e for stimulating the vagus nerve are positioned closer to the aortic arch. This embodiment might be even further modified as shown in FIG. 7C, so that a single array of electrodes 18d is used for both aortic arch baroreceptor stimulation and vagus nerve stimulation.

Figure 7D:
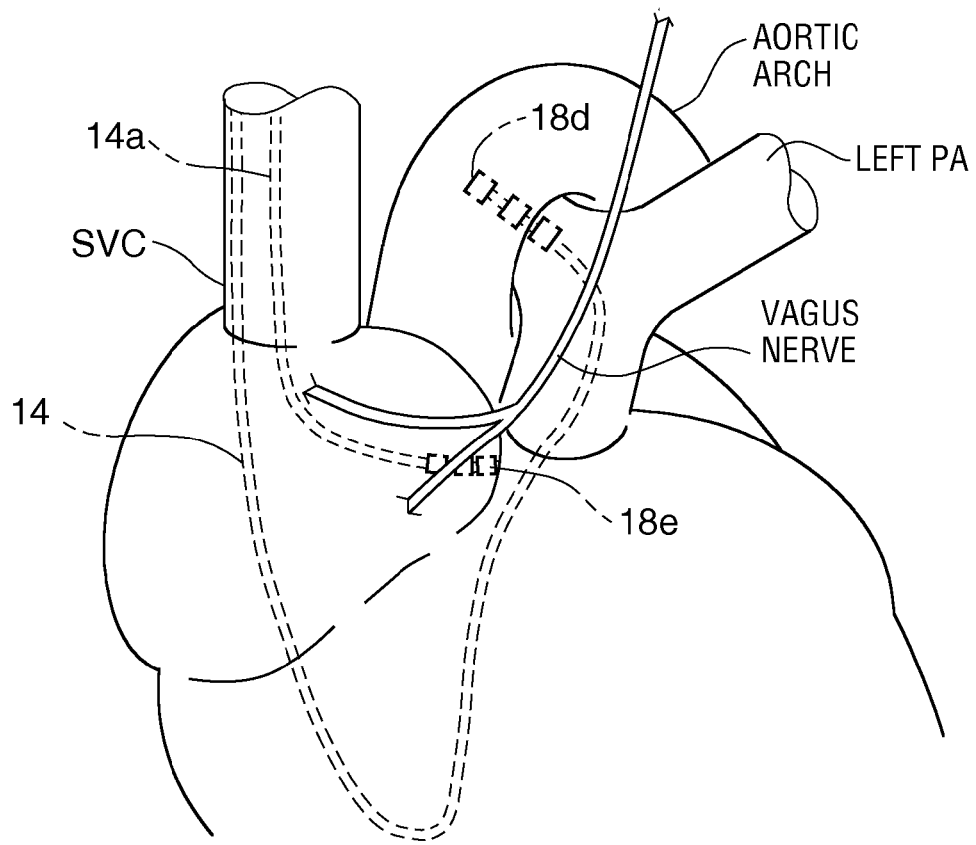

In the FIG. 7D embodiment, lead 14 is delivered to the pulmonary artery at the intersection with the aortic arch, to optimally position and anchor the stimulation electrodes 18e to stimulate the aortic arch baroreceptors. A second lead 14a is delivered to either the right atrium (shown) or to the right ventricle. Second lead 14a includes a separate set of stimulation electrodes 18e positioned and anchored to optimally stimulate the vagus nerve.

In any of the exemplary electrode/lead configurations, stimulation may be performed using the same energy delivery protocols for both aortic arch baroreceptor stimulation and vagus nerve stimulation. Alternatively, any of the lead/electrode configurations might utilize separate energy delivery protocols for stimulating the aortic arch baroreceptors and vagal nerve. Several ways in which this could be accomplished include: (a) interleaving/multiplexing (time sequencing where "A" therapy is on for a pre-determined or adaptively determined duration followed by a "B" therapy that is on for a predetermined or adaptively determined time in a repeating "A"/"B" sequence) the delivery of two separate electrical stimulation protocols utilizing the same stimulation electrodes or (b) having a multiplicity of electrodes on the lead such that one set of electrodes can be utilized to uniquely stimulate the carotid baro-response and a second set of electrodes can be utilized to uniquely stimulate the vagus nerve, these therapies would be independent of each other so could be delivered simultaneously but could also be sequenced as described in (a).

The therapy performed using the configurations of FIGS. 7A-7D can provide multiple benefits, including (1) activation of the baro-response to lower blood pressure, (2) activation of the parasympathetic afferent and efferent pathways to help rebalance the sympathetic/parasympathetic imbalance that is common in heart failure patients, (3) mild reduction in heart rate that can reduce total cardiac energy consumption, reduce diastolic pressures, reduce mean arterial pressures, and possibly reduce afterload.

The electrodes may be configured in a uni-polar, bipolar, tri-polar arrangement, or they may be arranged in an array for selective activation. Various configurations for anchoring or supporting the electrodes and lead may be implemented.

Figure 8A:
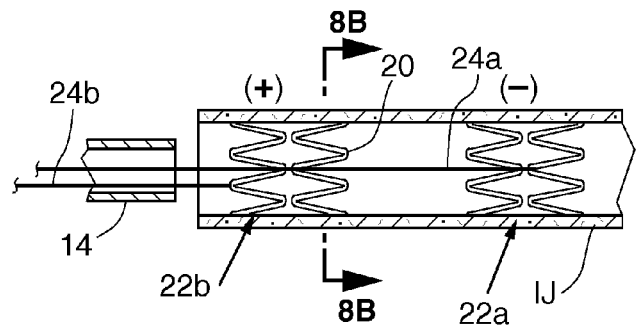
FIG. 8A is a side elevation of a first embodiment of an electrode and anchor structure. The electrode and lead are positioned in a vessel shown in cross-section.
Figure 8B:
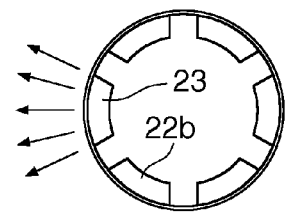
FIG. 8B is a cross-section view taken along the plane designated 8B-8B in FIG. 8A.

Referring to FIG. 8A, the anchor may take the form of a stent-type device 20 that is expandable into contact with the walls of the vessel to maintain its position with the vessel. Electrodes 22 are attached to, or integral with, the stent. The stent may be balloon expandable or self-expanding. Suitable stent materials include polymeric materials and/or metals. In the illustrated design, stent 20 is formed of discrete metallic segments. A distal one of the segments 22a functions as a negative electrode and a proximal one of the segments 22b functions as a positive electrode. Each of the segments 22a, 22b has a corresponding conductor 24a, 24b that extends through the lead 14 to pulse generator housing 12 (FIG. 1A). The segments 22a, 22b may be completely separate from one another as shown. In other embodiments, the segments may be coupled to or are integral with one another, in which case remaining portions of the stent (e.g. between the segments) are insulated or formed of non-conductive material. Additionally, as shown in FIG. 8B, a portion of the circumference of each electrode segment 22a, 22b is masked using an insulative polymeric coating such that the segment is conductive around less than its 360 degree circumference, allowing the stent to preferentially direct the electric field towards the target area from the unmasked region 23.

In another embodiment, a polymeric stent or non-conductive braid may be provided with electrodes mounted to it such that the electrodes are positioned in contact with the vessel wall when the stent or braid is expanded. For example, as shown in FIG. 9A, four distal electrodes 26a-d are positioned at 90 intervals around the circumference of a distal portion of braid 28, and four proximal electrodes 26e-h are similarly positioned. Conductor wires 30a-h (not all of which are visible) extend from corresponding ones of the electrodes 26a-h through the lead 14. Any number of techniques may be used for mounting the electrodes to the stent. In the embodiment shown in FIG. 9A, an adhesive is used to mount the electrodes to the outer circumferences of silicone rings 32a, 32b positioned within or surrounding the braid 28. The braid may be self-expandable, or it might employ an active expansion mechanism, such as an outer tube 34 mounted to the proximal end of the braid and an inner tube 36 mounted to the distal end of the tube such that the braid may be expanded by withdrawing the inner tube as shown in FIG. 9B. The inner tube 36 may include a guidewire lumen which allows the braid to be tracked over a guidewire for implantation.

Figure 9A:
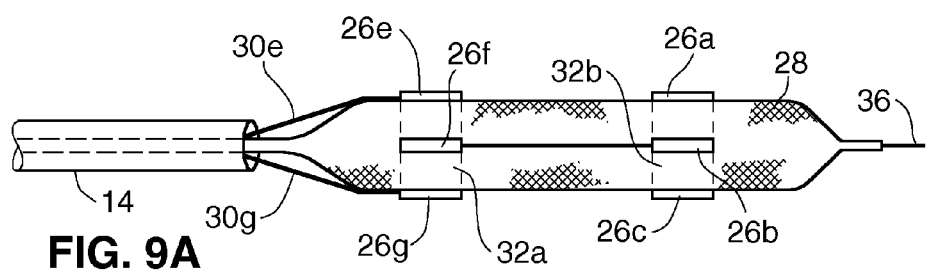
FIG. 9A is a side elevation view showing a second embodiment of an electrode and anchor structure.
Figure 9B:
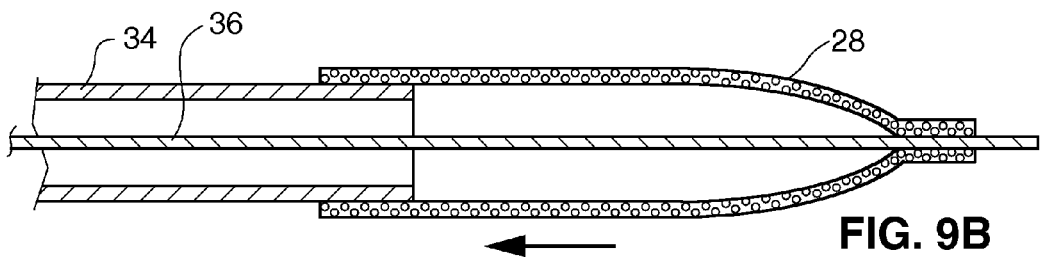
FIG. 9B illustrates the embodiment of FIG. 9A in the collapsed position.

In a modification to the FIG. 9A embodiment, electrodes external to the braid are positioned on wires that are woven through the braid. In yet another alternative, a stent or braid configuration may alternatively be expanded to "sandwich" separately introduced electrodes (e.g. electrodes mounted on a conductor positioned parallel to the braid) between the stent/braid and the vessel wall.

Figure 9C:
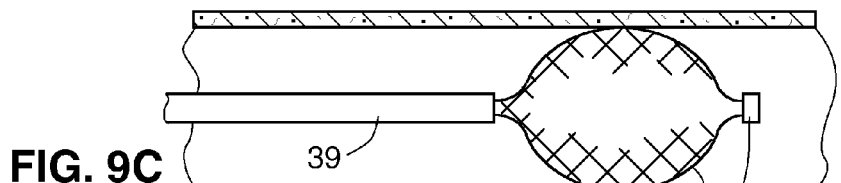
FIG. 9C illustrates an alternative to the electrode and anchor structure of FIG. 9A shown schematically in a mapping position within a blood vessel.
Figure 9D:
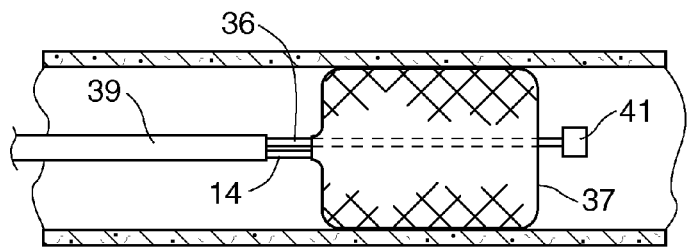
FIG. 9D is similar to FIG. 9C but shows the electrode and anchor in the fully deployed position.

FIGS. 9C and 9D illustrate an embodiment in which the anchor (with the electrodes coupled thereto as described) is configured to allow partial deployment for mapping purposes before the anchor is fully deployed at its final location. The anchor 37 is initially disposed within an introducer sheath 39. The distal end of the anchor 37 is contained within a tubular end cap 41. An inner tube or mandrel 36 extends through the sheath and the anchor and is attached to the tubular end cap 41. The introducer sheath 39 is advanced to a target position within the vessel and the anchor 37 is partially advanced from the introducer sheath 39. At this stage, the anchor 37 may be in a position similar to that shown in FIG. 9B with respect to the prior embodiment. The mandrel 36 is then moved proximally to expand the anchor into the partially deployed position shown in FIG. 9C. Mapping tests are performed by delivering stimulation energy from the electrodes on the anchor and measuring the response (e.g. blood pressure, heart rate, and/or related parameters). The mandrel is advanced distally to partially collapse the anchor and the anchor is moved to a second location. The anchor is re-opened to the partially deployed position as described above and additional mapping procedures are performed. The process is repeated until the anchor electrode position is optimized. The anchor is fully deployed by detaching the cap 41 from the distal end of the anchor (e.g. by rotation, electrolytic detachment or other means), thereby allowing the distal end of the anchor to fully expand. The mandrel 36 and introducer 39 are withdrawn, leaving the electrode anchor 37 and lead disposed in the vessel.

Figure 10A:
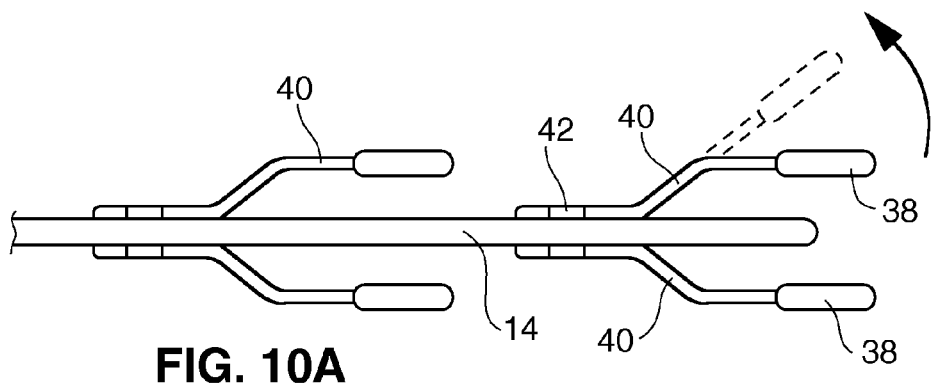
FIG. 10A is a side perspective view showing a second embodiment of an electrode and anchor structure.
Figure 10B:
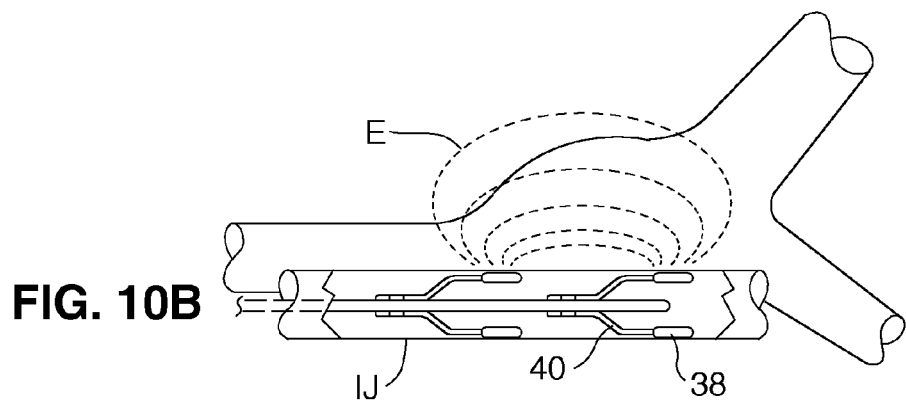
FIG. 10B schematically shows the FIG. 10A embodiment within a vein in proximity to a carotid sinus bulb. The vein is shown as transparent.

Alternative embodiments use structures other than stents or braids to support the electrodes against the vessel walls. For example, FIG. 10A illustrates an embodiment in which the electrodes 38 are supported by tines 40 that expand outwardly to position the electrodes in contact with the vessel wall. The tine and electrode shown in dashed lines illustrates the spring bias exhibited by the tines when they are not restrained by a sheath or vessel wall. Separate conductors 42 for each of the electrodes run through the lead 14. During implantation the physician will select the combination of electrodes that will cause the electric field to reach to the target neurological structures as shown in FIG. 10B.

Figure 11A:
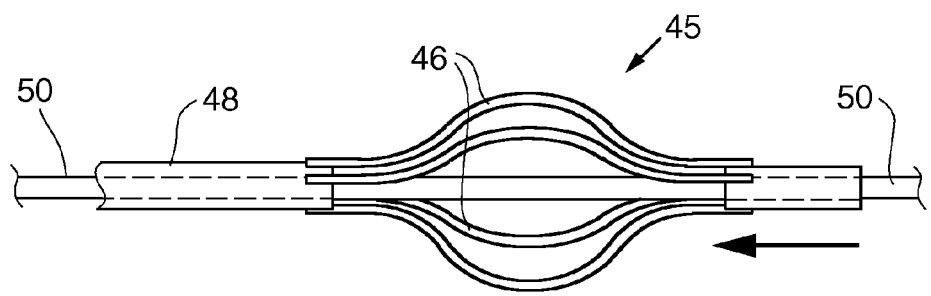
FIG. 11A is a perspective view of a third embodiment of an electrode and anchor structure.

In another alternative embodiment shown in FIG. 11A, an electrode carrying anchor 45 includes a collection of struts 46 coupled to an outer tube 48 at their proximal ends and to an inner tube 50 at their distal ends 50. The inner tube 50 extends through the outer tube 48 such that relative movement away from one another places the struts in an elongated position for passage through the vasculature. Relative movement of the tubes 48, 50 towards one another causes the struts to expand outwardly into contact with a vessel wall when a delivery sheath restraining the struts is withdrawn or removed. Each strut may itself function as an electrode insulated from the other struts, and the struts which are to be energized may be determined in a mapping procedure. In other embodiments several of the struts of an anchor may be insulated, with the remaining struts conductive and operable as electrodes. Alternatively, sections of conductive struts may be masked off to leave one or more conductive regions. In other embodiment, electrodes may be mounted to the struts such that expansion of the struts positions the electrodes into contact with the vessel wall.

Figure 11B:
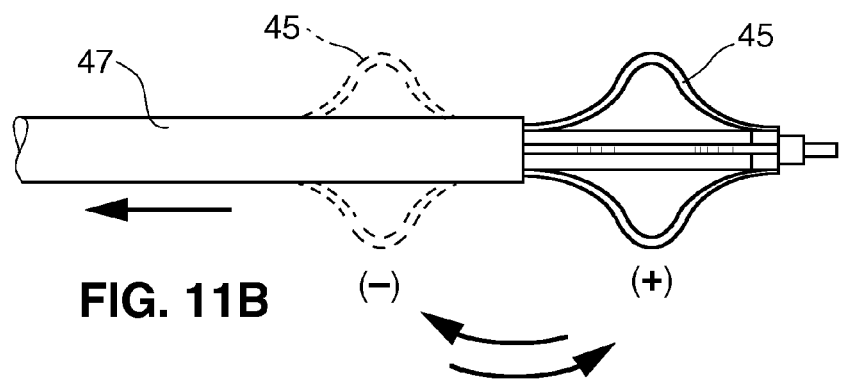
FIG. 11B illustrates sequential deployment of two units of the electrode/anchor of the FIG. 11A embodiment.

FIG. 11B illustrates that a pair of the FIG. 11A devices 45 may be deployed in sequence from a sheath 47 within a blood vessel. In the drawing, the second of the two devices 45 has not yet been deployed, but its intended position following deployment is shown in dashed lines. These electrode anchor devices are coupled to the pulse generator such that one of the devices 45 functions as the negative electrode and the other functions as a positive electrode.

Figure 12A:
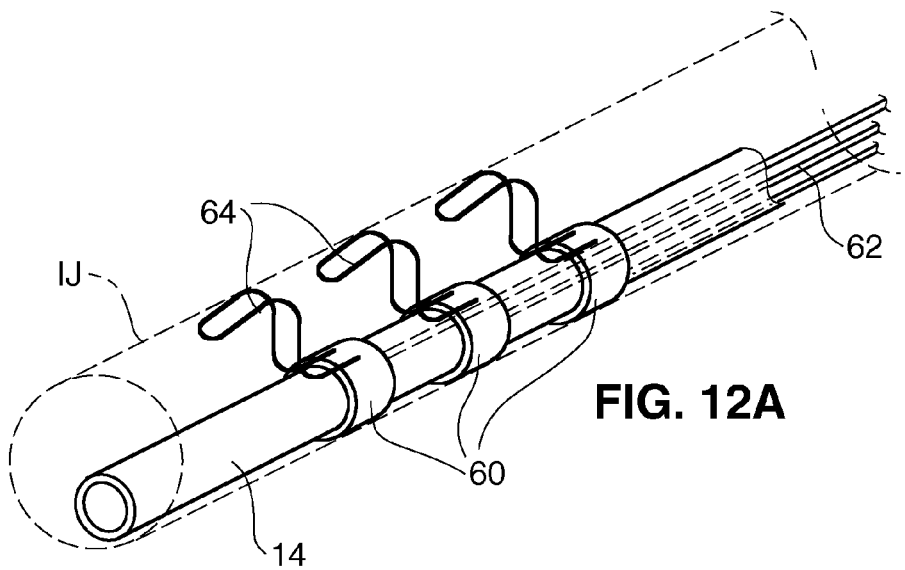
FIG. 12A is a perspective view showing a fourth embodiment of an electrode and anchor structure, the electrode and anchor are shown positioned within a vessel which is illustrated as transparent.
Figure 12B:
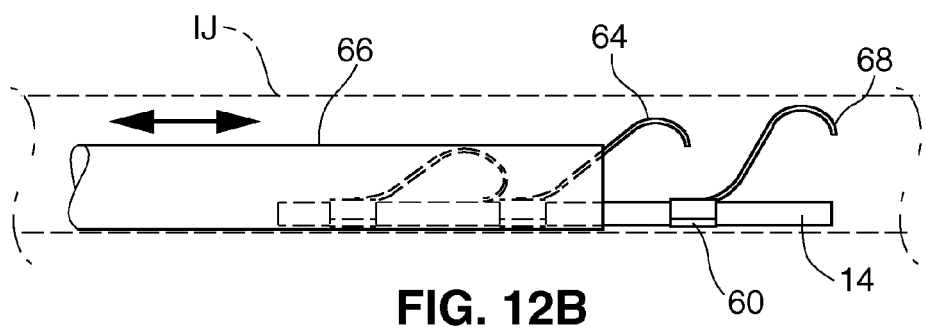
FIG. 12B shows the fourth embodiment of FIG. 12A partially positioned within a deployment sheath.
Figure 12C:
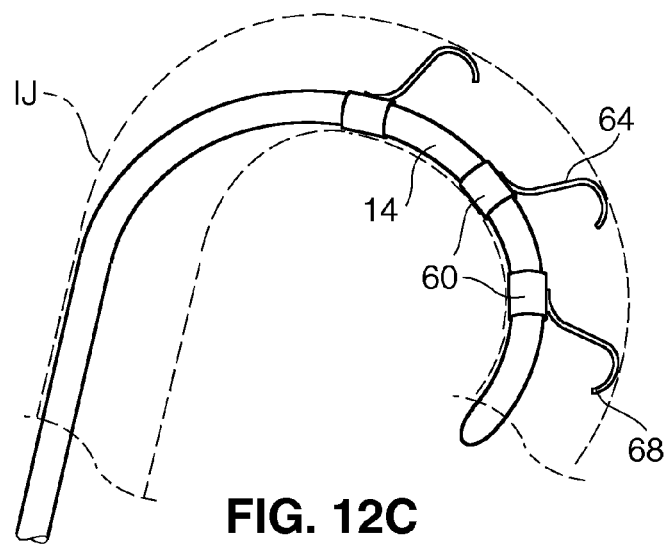
FIG. 12C shows the fourth embodiment of FIG. 12A deployed in a blood vessel which is shown as transparent.

FIGS. 12A through 12C illustrate an alternative design of an electrode and anchoring device designed to push the electrodes into contact with the vessel wall (shown in dashed lines in the drawings). This embodiment is advantageous is that it is re-sheathable into a catheter within the body, allowing repositioning of the electrodes if necessary to gain better access to a stimulation target. Referring to FIG. 12A, lead 14 includes a plurality of band electrodes 60, each having an insulated conductor wire 62 extending through the lead. A plurality of nitinol spring members 64 extend from the lead 14 and include a free end 68 formed to have an atraumatic curvature. As best shown in FIG. 12B, when the lead 14 is positioned within a deployment sheath 66, spring members 64 are compressed such the free ends 68 are moved towards the lead 14. When the lead 14 is advanced from the sheath 66, the free ends spring outwardly into contact with the vessel wall, thereby pressing the electrodes 60 into contact with an opposite side of the vessel wall. The spaced apart positioning of the spring members allows electrode contact with the vessel wall to occur even when the electrodes are situated within a bend in the vessel as shown in FIG. 12C.

Figure 13:
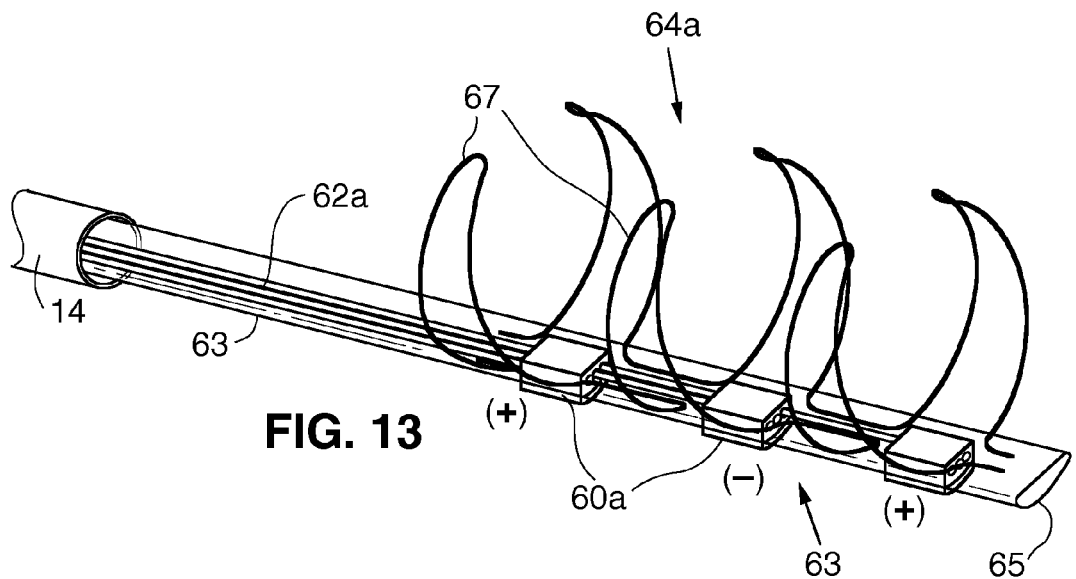
FIG. 13 is a perspective view of an alternative electrode and anchor arrangement.

In another embodiment of an electrode anchor device shown in FIG. 13, an array of electrodes 60a is disposed on an elongate member 63. The member 63 is formed of flexible substrate (e.g. silicone). The member is preferably shaped to have a convex face 67 positionable in contact with the vessel wall. The substrate encapsulates the distal portions of the conductors 62a and partially encapsulates the electrodes 60a, leaving the electrodes exposed on the convex face 67 for contact with the interior of the vessel wall. The electrodes include pass through lumens 65 which allow the conductors 62a to be routed through electrodes rather than routed around them.

In an alternate embodiment, the electrodes may instead be formed onto or attached to one face of the member 63.

The anchor 64a is comprised of one or more resilient elements 67 extending laterally from the member 63. The resilient elements are preferably curved so as to extend partly or fully circumferentially along the vessel wall. In the illustrated embodiment, nitinol wires are shaped to include a plurality of v-shaped hoop sections defining the resilient elements 67, with each member curving outwardly from its origination at the substrate and then curving inwardly to give the member a partially circumferential shape. Two such wires are shown, each defining three opposed elements 67. In other embodiments, each element may be discrete from the other elements. In still other embodiments, the elements may be more fully circumferential (e.g. hoops of the type shown in FIG. 18).

Figure 14:
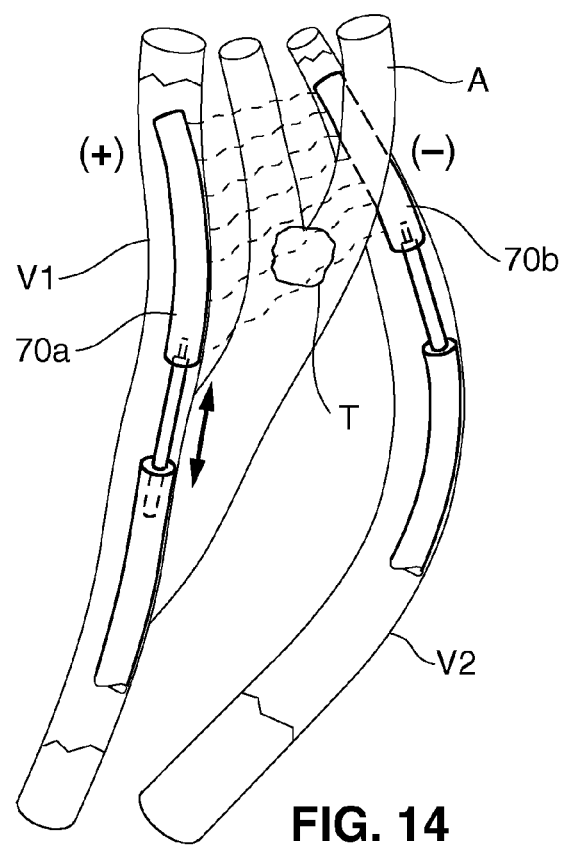
FIG. 14 schematically illustrates a pair of electrodes positioned in separate veins on opposite sides of a target neurological structure.
Figure 17:
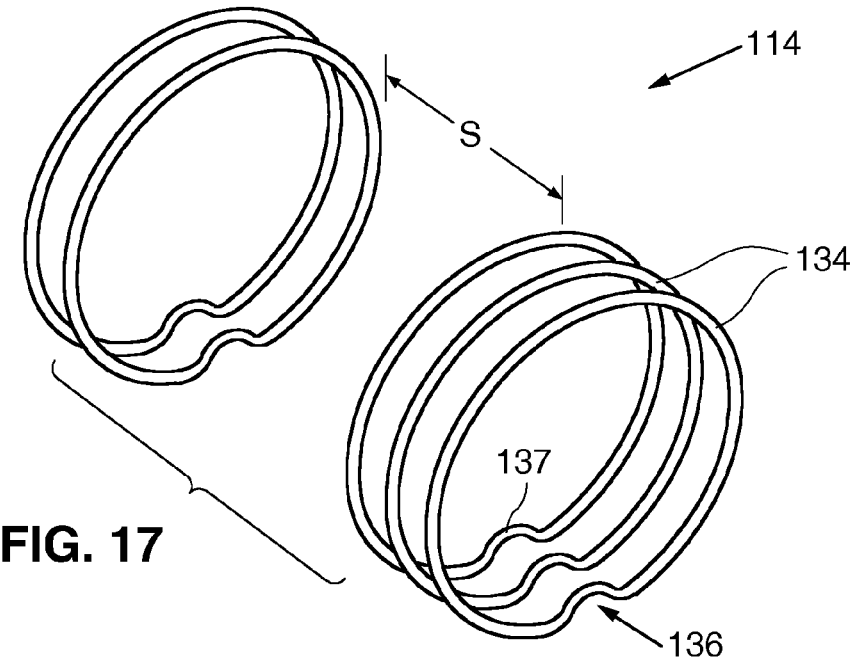
FIG. 17 is a perspective view of the anchor of FIG. 15.

As illustrated in FIG. 14, in an alternative embodiment, separate electrodes are placed in separate veins V1, V2 positioned on opposite sides of the nerve structure or baroreceptor T that is the target of the stimulation energy. In this embodiment, electrode structures such as those described above may be used. Alternatively, the electrodes 70a, 70b may instead be elongate sections of conductive wire or ribbon having a small cross-section that allows access to smaller vessels. As illustrated by the field lines in FIG. 13, activation of electrodes in this arrangement allows the electric field to extend from one vessel to the other. The positioning of the electrodes is tine-tuned as indicated by arrows by adjusting the longitudinal position of each electrode in its corresponding vessel, such that the generated field passes through the target neurological structure T.

FIGS. 15 through 22 illustrate an alternative intravascular anchor having a lead that may be detached from the anchor in situ, allowing explantation of the lead while leaving the anchor in place within the blood vessel. When a lead is chronically implanted within a blood vessel, tissue or other material may grow, form or accumulate on parts of the device (e.g., through cellular encapsulation, in-growth, endothelial-ization, thrombosis, etc.). When it is time to remove a lead from the patient, the tissue growth may complicate the extraction process, particularly with respect to the anchor which is in contact with the vessel wall. In some instances, it may be desirable to separate the lead from the anchor and to extract the leads while leaving the anchors in the blood vessel, so as to minimize the risk of damage to the vessel wall. The FIG. 15 through 22 embodiments show a lead and anchor system that permits extraction of a lead while leaving the associated anchor behind. The following discussion also describes a method for detaching a lead from an anchor, and for optionally replacing the explanted lead with a new lead.

These embodiments are shown and described with respect to electrical leads for use in delivering electrical stimulation to nervous system targets as discussed above, or to tissue of the heart, using electrodes. However it is to be understood that these concepts may be used for leads that take the form of fluid conduits for delivery of therapeutic or diagnostic agents. In still other embodiments, the leads may be used for communication of signals representing parameters sensed within the vasculature using sensors on the leads.

Referring to FIG. 15 system 100 generally includes an anchor 114, a lead 116, and an electrode array 118 on the lead 116. Array 118 includes a plurality of electrodes 120a-c. In FIG. 15, a blood vessel W is schematically illustrated surrounding the anchor 114.

Lead 116 includes an elongate cable 122 which houses conductors 124a-c that are electrically coupled to the electrodes 120a-c. A member 126 formed of flexible substrate (e.g. silicone) encapsulates the distal portions of the conductors 124a-c and partially encapsulates the electrodes 120a-c, leaving exposed faces 132 on one side of the member 126. The electrodes are provided with pass through lumens 134 which allow the conductors 124a, 124b to be routed through electrodes rather than routed around them.

In an alternate embodiment, the electrodes may instead be formed onto or attached to one face of the member 126.

Anchor 114 is preferably an expandable device radially compressible into a collapsed position for loading into a deployment sleeve for intravascular introduction into a target blood vessel. The device is radially expandable upon release from the deployment sleeve, so that it can expand into contact with the wall of the blood vessel W at a target site. The anchor has structural features that allow it to radially engage the vessel wall using forces sufficient to maintain the positioning of the anchor at the target site, but not necessarily sufficient to perform the functions of a stent. The anchor might be a tubular band, sleeve, mesh, braid, laser cut tube, or other framework formed of one or more shape memory (e.g. nickel titanium alloy, nitinol, thermally activated shape-memory material, or shape memory polymer) elements or stainless steel, Elgiloy, or MP35N elements.

The anchor 114 includes a receiver 136 positioned to receive the member 126 so that the electrodes supported by the member are retained at a desired position within a blood vessel. In the embodiment shown in FIGS. 15-18, the anchor 114 includes a plurality of hoops 134 in which a portion of the hoop 134 curves radially inwardly and then outwardly to define a receiver section 137. The hoops 134 are positioned in the vessel W such that the receiver sections 137 are longitudinally aligned as shown in FIG. 15, thus forming receiver 136 bounded by the receiver sections 137 of the hoops on the radially inward side and by the vascular wall W on the radially outward side. The receiver 136 is dimensioned to slidingly receive the member 126 and to support it within the vessel W as shown in FIG. 15, so that the exposed sections 132 (FIG. 18) of the electrodes are biased in contact with the vessel walls.

The hoops 134 may be individual hoops positionable in a spaced apart arrangement within the blood vessel. In the FIG. 15-18 embodiment, the hoops 134 are arranged in a proximal grouping and a distal grouping, wherein the proximal and distal groupings are separated by an elongate space S. The space S may equal or exceed the longitudinal separation distance between the distalmost portion of the most distal electrode in the array and the proximalmost portion of the most proximal electrode. Although the illustrated proximal and distal groupings include two hoops in the distal grouping and three hoops in the proximal grouping, other numbers of hoops may be used. In another embodiment, either or both of the proximal and distal groupings may include only a single hoop.

In other embodiments all of the hoops, or each of the proximal and distal groupings of the hoops, may be coupled together by struts, a sleeve, or other elements made from polymeric material, ePTFE, or other suitable materials. In the embodiment shown in FIGS. 19 and 20, longitudinal struts 138 extend between the hoops 134. These struts 138 are disposed in the receiver sections 136, and bow slightly outwardly at their midsections, helping to bias the member 126 and thus the electrode sections 132 into contact with the wall of the surrounding vessel V. Tabs 140 are optionally positioned on the proximal end of the struts 138 and can be used for docking a lead removal device as will be described below.

To deploy the system 100, the anchor 114 is radially compressed into a collapsed position and loaded into a deployment sleeve. Using known techniques, the deployment sleeve is percutaneously introduced into the vasculature and advanced to the target blood vessel where the electrodes are to be anchored. The anchor 114 is released from the deployment sleeve and allowed to expand within the vessel. Where the anchor 114 is comprised of separate hoops, the anchor may be released in sequential steps in which a distalmost one of the hoops 134 is pushed from the deployment sleeve, and the deployment sleeve is then withdrawn slightly. The next one of the hoops 134 is pushed from the deployment sleeve into the vessel, and the process is repeated for each of the hoops. The amount by which the deployment sleeve is withdrawn after each hoop is released determines the spacing between the hoops.

Figure 18:
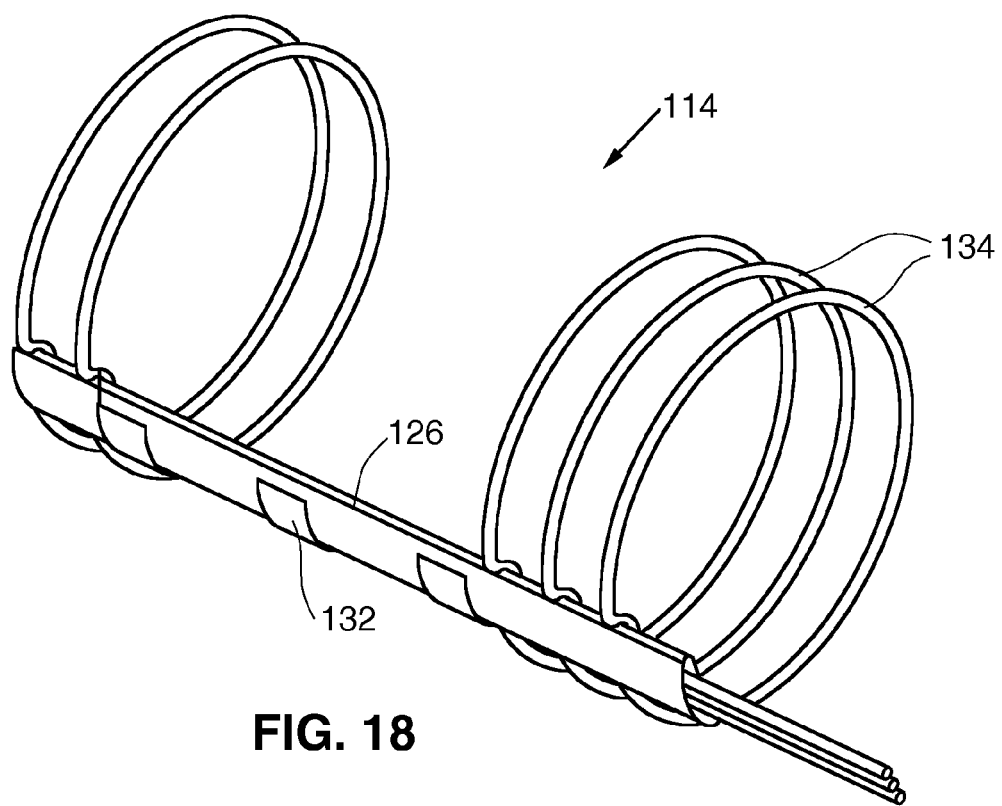
FIG. 18 is a perspective view of the lead and anchor system with the electrode member disposed in the receiver and with the assembly rotated to show the exposed surfaces of the electrodes.
Figure 19:
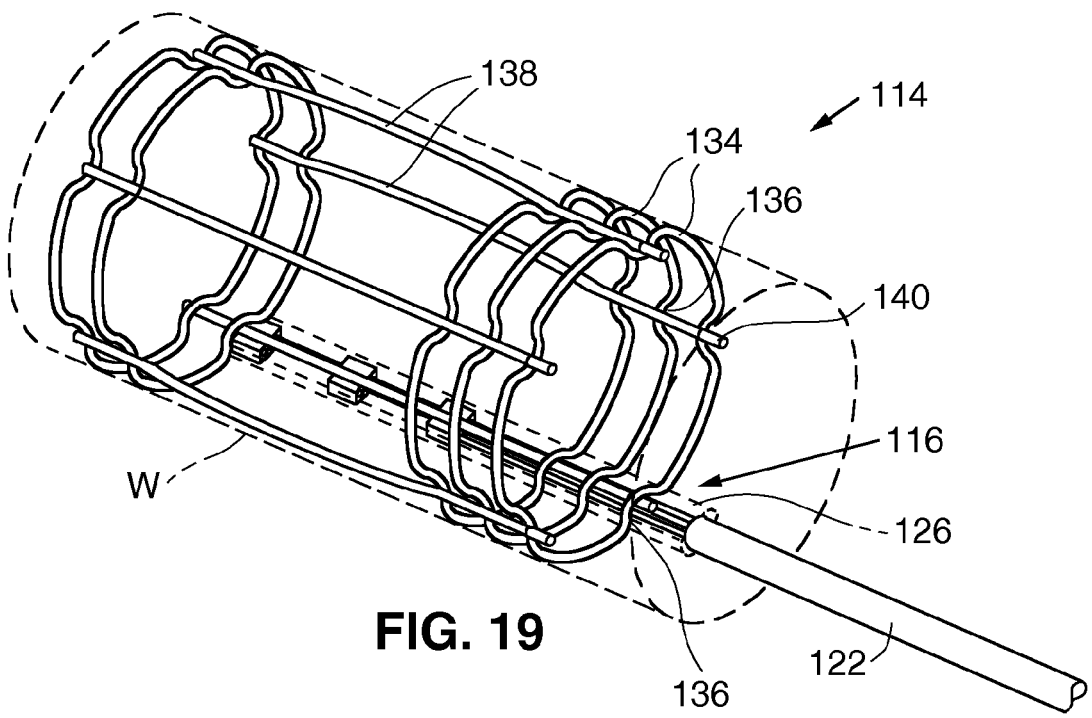
FIG. 19 is a perspective view showing a slightly modified embodiment of an anchor and lead system in which a portion of a blood vessel is schematically shown around the anchor. The anchor is schematically shown disposed within a portion of a blood vessel, the walls of which are shown as transparent.
Figure 20:
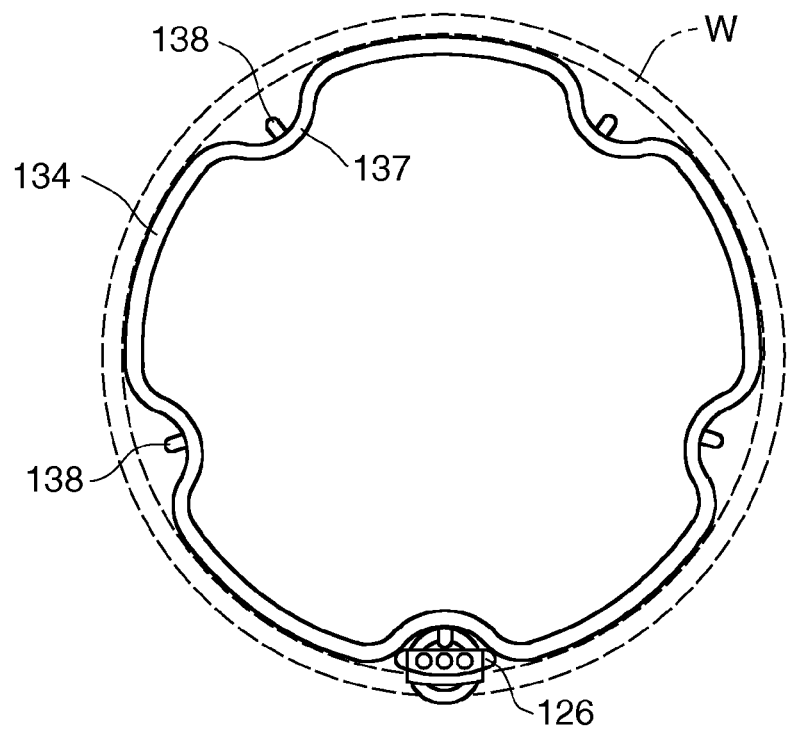
FIG. 20 is a distal end view of the anchor and lead of FIG. 19 shown disposed within the vessel to illustrate positioning of the electrode between the anchor and the vessel wall.

Once the anchor 114 is deployed, the member 126 is advanced into the receiver 136 as indicated by arrow A1 in FIG. 15, and it is advanced distally to position the member 126 within the receiver as shown in FIG. 19. The member 126 is retained within the vessel between the anchor 114 and the vessel wall as shown in FIG. 20. When the member 126 is in the retained position, the exposed faces 132 of the electrodes preferably face outwardly as shown in FIG. 18, such that they are in contact with the surrounding vessel wall.

At times it may be necessary to remove the lead from the anchor. For example, lead removal might be desirable if the electronic device energizing the electrode is no longer in use, or because the lead is not functioning properly and should be replaced. FIGS. 21-25 illustrate a method for removing the lead 116 from the anchor 114. When lead removal is needed, a lead removal/exchange catheter is advanced over the proximal end of the lead cable 122. This step may be achieved by detaching a proximal portion of the lead from the device body 12 (FIG. 1), and then passing the removal catheter over the free end of the lead. When the distal end of the removal catheter has reached the anchor 114, it may be coupled to a proximal portion of the anchor 114, such as the tabs 140 or another feature, so as to dock the removal catheter to the anchor.

A guidewire is passed through the retrieval catheter and into the receiver 136 within which the distal portion of the lead (at member 126) is disposed. The retrieval catheter is held in place while the lead 116 is withdrawn into it using tension applied to the proximal end of the lead 116.

If a new lead is to be introduced into the receiver 136, the old lead may be fully withdrawn from the retrieval catheter and out of the body, leaving the catheter in place for use in providing a passage for the new lead into the vessel. Alternatively, the retrieval catheter with the old lead inside it may be withdrawn from the body, leaving the guidewire in place. A second catheter is advanced over the guidewire and (optionally) docked to the anchor as described above. The replacement lead is advanced distally through the catheter and inserted into the receiver 136.

In an alternate arrangement, the member 126 of the lead 116 is provided with an opening that may be threaded over the guidewire, allowing the lead 116 to be tracked over the wire into the receiver 136. The opening may be a bore formed in the material of the member, or it may be a loop of suture or other material that is coupled to the member.

Figure 21:
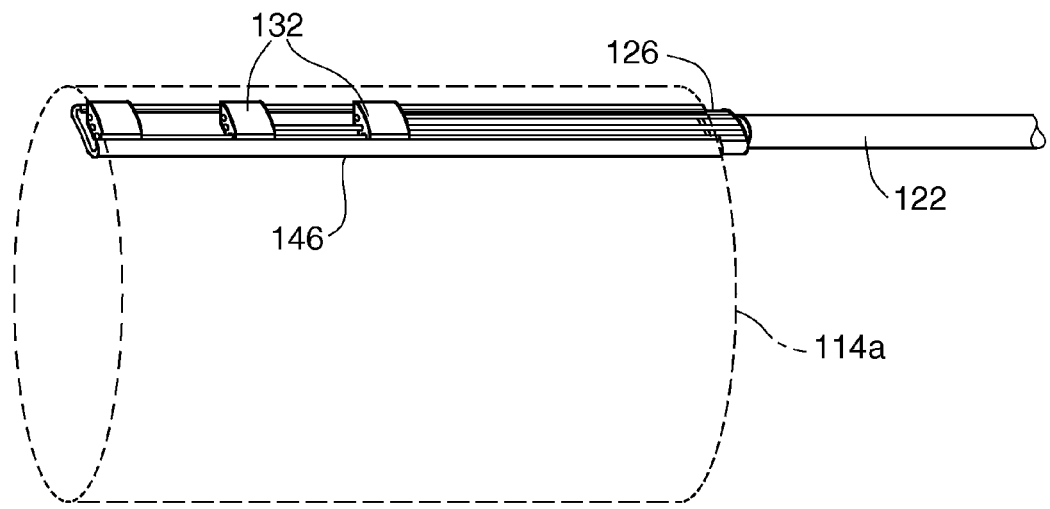
FIG. 21 is a perspective view of an alternate embodiment of a lead and anchor system.
Figure 22:
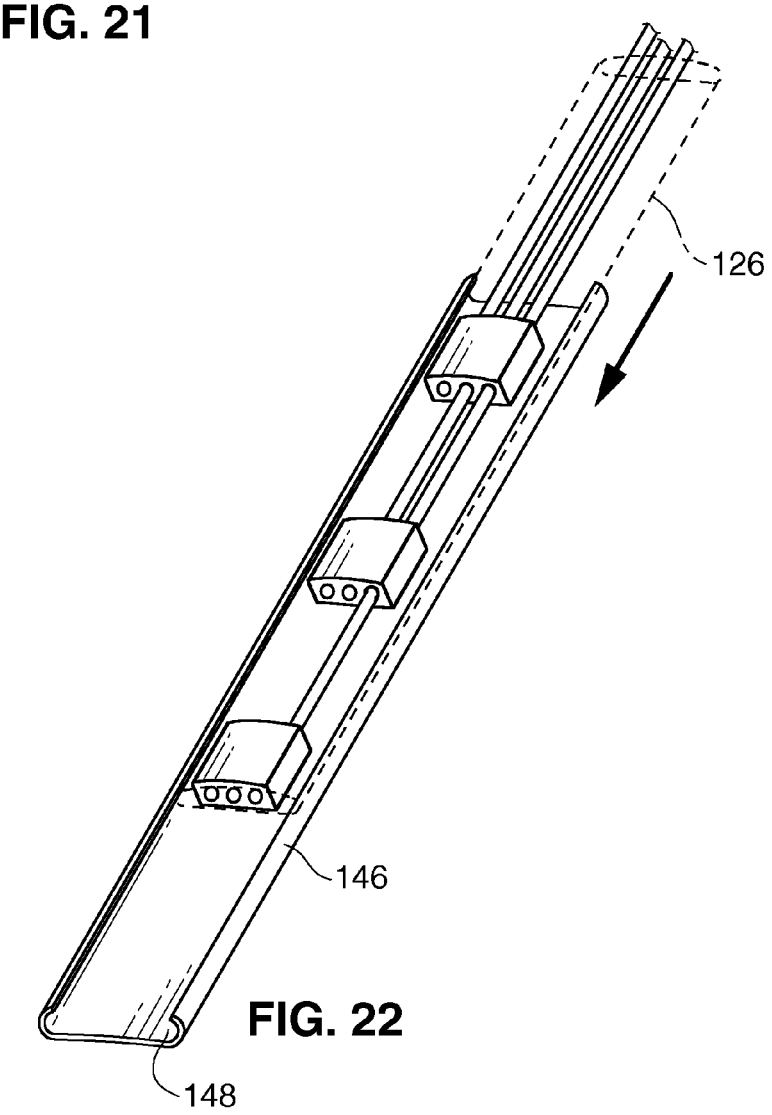
FIG. 22 is a perspective view of the receiver of the embodiment of FIG. 21, showing insertion of the electrode member into the receiver.

FIG. 21 shows an alternative embodiment using a modified form of receiver on an anchor 114*a*. In this embodiment, the receiver 146 comprises an elongate member having a longitudinally extending channel 148. The receiver is proportioned to receive the flexible member 126 of the lead 116 within the channel 148 such that the exposed surfaces 132 of the electrodes face outwardly towards (and ideally in contact with) the vessel wall.

The elongate member is mounted to or formed on the anchor, such as on the inner or outer wall of the anchor. It is preferably inwardly recessed from the radially outermost boundary of the anchor (as with the receiver 136 of the first embodiment) so that the exposed surfaces 132 will be generally flush with or inset from the exterior of the anchor when the anchor and lead are implanted. However in other embodiments, the configuration may be such that the exposed surface are positioned radially outwardly of the exterior surface of the anchor. The anchor 114*a* may take any of the forms disclosed above. The member 126 is insertable into and removable from the receiver 146 as described above, allowing explantation and or replacement of the lead while the anchor remains in the vessel.

Figure 23A:
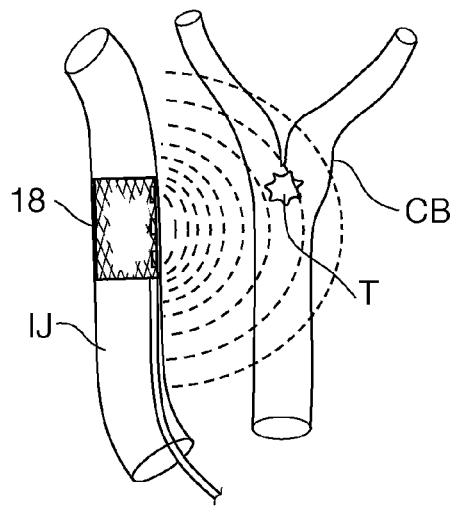
FIG. 23A schematically illustrates an electric field passing from a stimulation electrode in the internal jugular vein.
Figure 23B:
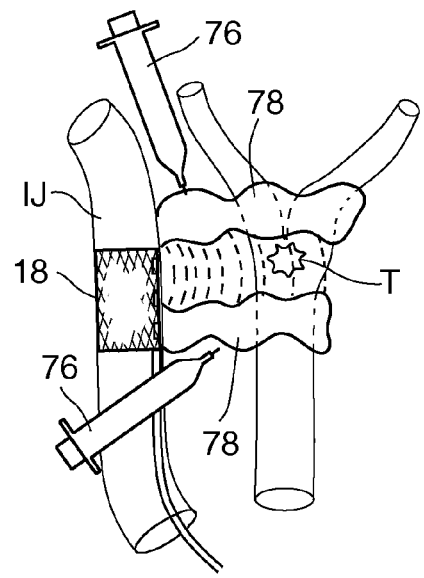
FIG. 23B illustrates administration of a steering insulative material to steer the electrode field of an electrode positioned as in FIG. 23A.

In the disclosed embodiments, optimal stimulation results are achieved when the electrodes are positioned to direct the stimulation energy towards the neurological target while minimizing conduction of the energy to unintended targets. As shown in FIG. 23A, the electric field patterns from a stimulation electrode 18 within the internal jugular can extend through a broad area, creating unwanted collateral stimulation of nerves other than the target structures T, possibly causing unintended physiological responses. Referring to FIG. 23B, syringes 76 may be passed through the skin and used to inject insulative steering materials 78 into the space between the jugular vein and the carotid artery, creating a shield protecting areas away from the target area T from collateral stimulation. In one example, fatty material (which may be fat extracted from the patient's own body) is used to create the shield. Alternate examples of injectible materials include silicone or other biocompatible insulating materials, including thixotropic materials (which have low viscosity when subjected to stresses during injection using a syringe, but which increase in viscosity once injected) and polymers that may be cured using light, energy, or other substances following injection.

The injected material forms or defines a channel 80 between the jugular and the carotid artery. The channel provides a conductive path for current passing from the electrode to the region of the carotid artery. In other embodiments, rather than being used to form a channel, the injected materials may be injected onto specifically identified muscles or nerves for which collateral stimulation is undesired. In these embodiments, the injected polymers or other materials form an insulative blanket or cover over the identified muscles or nerves to prevent the electrical stimulation from causing adverse side effects resulting from stimulation of those muscles or nerves.

Fluid substances or materials may alternatively be delivered onto the interior or exterior surface of a vessel containing the stimulation electrodes (e.g. the internal jugular vein) as a way of shielding portions of the vein circumference so that the simulation energy will only conduct through the unshielded portions of the vessel. Such materials may also or alternatively be delivered onto the interior or exterior surface of a vessel other than the vessel containing the electrodes (e.g. a vessel targeted by or in the path of the stimulation energy, such as the carotid artery), in order to limit conduction of stimulation energy beyond a desired region of that vessel.

Figure 24:
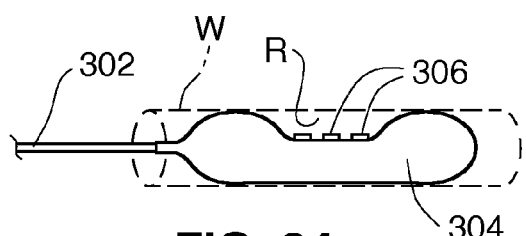
FIG. 24 schematically illustrates a method of administering an insulating material to an interior surface of a vessel wall.

The delivered materials or substances may be insulative polymers of the type described above, or they may be materials which cause modification of the vessel tissue (e.g. necrosis, ablation) to reduce the conductivity of the vessel tissue in areas through which conduction of stimulation energy is undesirable. Methods for delivering the materials include introducing a catheter 302 to the target site as shown in FIG. 24. The catheter includes distally positioned pores or other delivery ports 306 around a portion of its circumference. The ports are preferably on a balloon 304 carried by the catheter but they may be on the catheter itself. The balloon may be shaped such that the ports are located a reduced diameter portion of the balloon, so that the exterior of the balloon in this location will form a reservoir R between the vascular wall W and the balloon wall as shown in FIG. 24, allowing the injected material to accumulate in that portion of the vessel during curing. Radiopaque markers on the catheter and/or balloon may be positioned to identify the region of the balloon having the ports. The balloon is positioned at the delivery site and longitudinally and axially positioned such that the delivery ports are positioned to direct the substance onto the tissue through which electrical conduction is desired to be blocked. Light or other energy may be delivered through the balloon wall onto the material using an energy source 308 positioned within the balloon.

Figure 25:
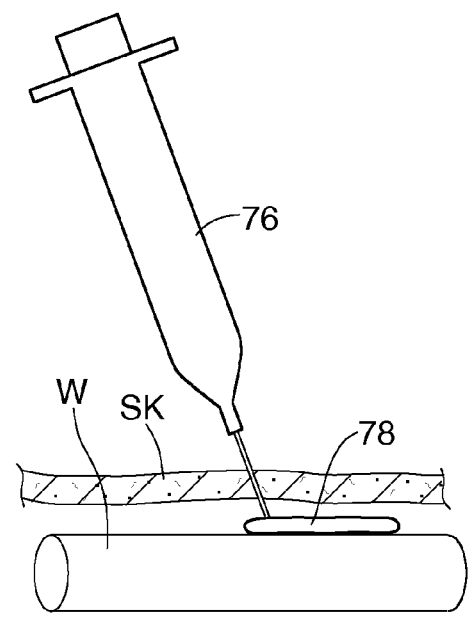
FIG. 25 schematically illustrates a method of administering an insulating method to an outer surface of a vessel wall.
Figure 26A:
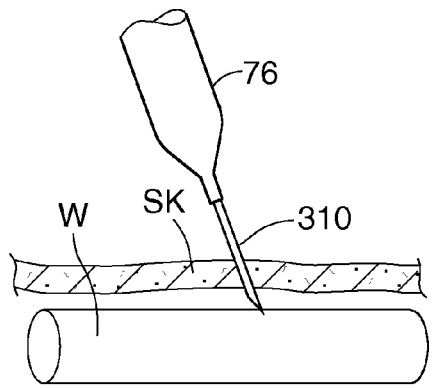
FIGS. 26A-26D are a sequence of drawings schematically illustrating placement of a shield in proximity to a vessel.
Figure 26B:
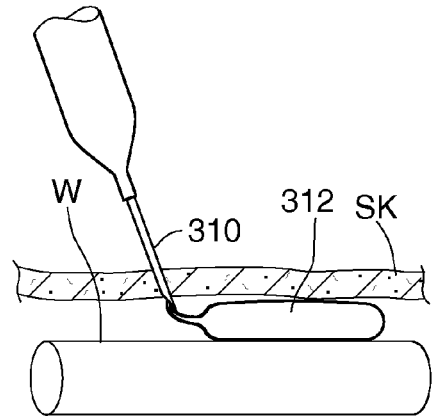
Figure 26C:
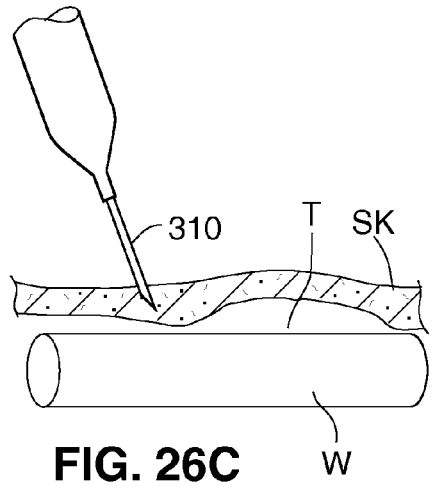
Figure 26D:
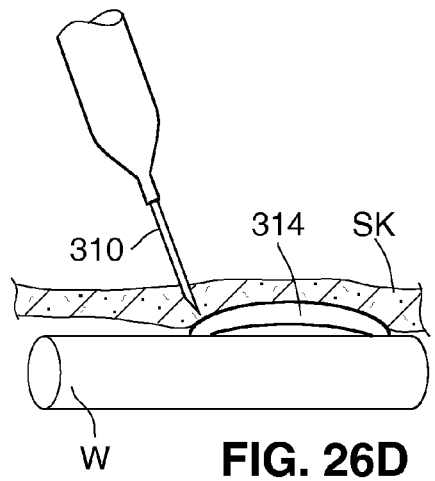

In an alternative method, a polymeric material 78 may be delivered onto the exterior surface of the vessel W using a needle 76 passed through the skin as shown in FIG. 25.

In another exemplary shielding technique, a minimally invasive surgical technique is used to implant an insulative shield surrounding the exterior wall of vessel W. The shield may be formed of a thin flexible insulative sheet or member positioned on or around the vessel exterior. In one exemplary method for implanting the member shown in FIGS. 26A-26D, a small incision or is formed to give access to the target vessel (e.g. the carotid artery or internal jugular). An access cannula 310 may be positioned within the incision to provide access for other instruments. A dissecting balloon 312 is introduced through the access cannula 310 and used to dissect the region surrounding the target vessel, creating a tunneled space T. The shield 314 is delivered to the tunneled space T via the access cannula 310. Other instruments passed through the access cannula 310 (or separate incisions) may be used to secure the shield 314 using sutures, tissue adhesives, or other means. The shield 314 may be wrapped or curled fully or partially around the vessel circumference, depending upon the area of vessel tissue that is to be shielded. The shield may be wrapped around the carotid artery or the internal jugular vein.

In alternate procedures, such a shield may be implanted through a small incision formed in the skin of the neck and wrapped around fully or partially around the carotid sheath.

Figure 28:
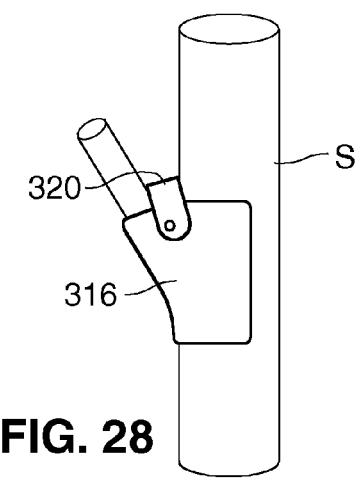
FIG. 28 illustrates an insulative shield positioned partially surrounding the carotid sheath to block transmission of stimulation energy to structures external to the carotid sheath.

For example, a shield 316 may be positioned partially or fully surrounding the carotid sheath S as shown in FIG. 28 to block conduction of the stimulation energy beyond the sheath. The shield may be a sheet of flexible insulative material as shown, or it may be a substance applied to the outer surface of the sheath or an insulative substance injected into the surrounding space. In the FIG. 28 example, a suture loop or other connector 320 may passed through the bifurcation between the sheath and the fascial tube containing the external carotid artery. The shield can be made of a material that is highly elastic so as to prevent constriction of the contents of the carotid sheath.

Other exemplary shielding methods may include chemical or electrical ablation of nerve or muscle tissue to minimize conduction of electrical stimulation energy to those tissues so as to minimize collateral stimulation effects such as muscle twitches.

Figure 27:
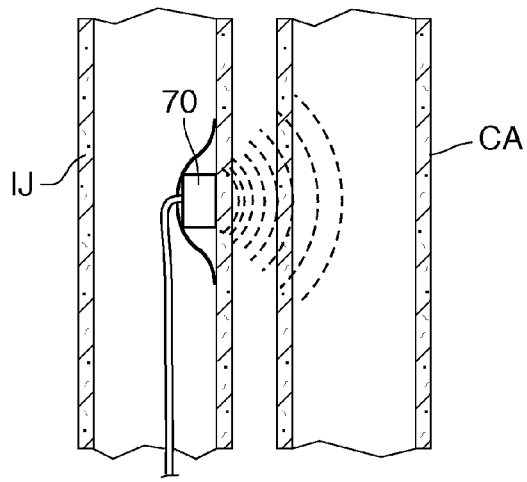
FIG. 27 illustrates an alternative embodiment utilizing ultrasound stimulation energy.

Although the majority of this description has been devoted to the use of electrical energy to stimulate the nervous system targets, FIG. 27 shows that the system 10 of FIG. 1A may be modified to replace the electrodes with an ultrasonic transducer or transducer array 70 that will produce acoustic or ultrasonic energy, shock waves, vibration, etc. The transducers are positioned at a location within the internal jugular that allows a focused pressure wave to impinge upon the carotid sinus, causing vibrations to simulate stretching of the vessel walls. Detection of a simulated wall stretch by the baroreceptors will prompt vasodilation, heart reduction and thus blood pressure reduction. Alternatively, direct ultrasound stimulation of nervous system targets may be utilized. In either case, certain ones of the transducers may be employed to cancel the effect of energy from others of the transducers as a means for minimizing the amount of energy propagating to non-targets. In other embodiments, transducers may be arranged to produce intersecting waves of intensity and phase that will combine to produce a therapeutic dose.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents. The terms "first," "second" and the like, where used herein, do not denote any order, quantity, or importance. In references to "first blood vessel", "second blood vessel" etc., the first and second blood vessels may be different blood vessels or they may be the same blood vessel unless otherwise specified.

Any and all patents, patent applications and printed publications referred to above, including patent applications identified for purposes of priority, are incorporated herein by reference.

The invention claimed is:

1. A method of implanting an intravascular electrode, comprising:
   percutaneously introducing an electrode system into a vasculature, the electrode system comprising an expandable anchor and at least one electrode on the anchor, the anchor having a radially compressed position and a radially expanded position;
   with the anchor in the compressed position, intravascularly advancing the electrode system to a first site in a target blood vessel;
   at the first site, expanding a first portion of the anchor to the expanded position while maintaining a second portion of the anchor in the compressed position, wherein expanding the first portion moves the electrode into contact with a wall of the target blood vessel;
   activating the electrode at the first site and measuring a change in physiological parameter indicative of stimulation of a nervous system target;
   intravascularly advancing the electrode system from the first site to a second site in the blood vessel;
   activating the electrode at the second site and measuring a change in physiological parameter indicative of stimulation of a nervous system target;
   selecting the first site or the second site as a chronic implantation site for the electrode; and
   with the electrode system at the chronic implantation site, expanding the second portion of the anchor to the expanded position to chronically retain the electrode at the chronic implantation site.

2. The method of claim 1, wherein intravascularly advancing the electrode system from the first site to the second site includes collapsing the first portion of the anchor, repositioning the electrode system, and then expanding the first portion of the anchor to move the electrode into contact with a wall of the target blood vessel at the second site.

3. The method of claim 1, wherein maintaining the second portion of the anchor in the compressed position includes maintaining the second portion within a tubular member.

4. The method of claim 1, wherein the method includes positioning the electrode system with the anchor in the compressed position within a sheath, and wherein expanding the first portion of the anchor includes deploying the first portion from the sheath to cause expansion of the first portion.

5. The method of claim 4, wherein maintaining the second portion of the anchor in the compressed position includes maintaining the second portion within a tubular member while the first portion is deployed from the sheath.

6. The method of claim 5, wherein the second portion comprises the distal end of the anchor and the first portion is proximal to the second portion.

7. The method of claim 1, wherein introducing the electrode system includes introducing a tubular stent-like anchor.

8. The method of claim 1, wherein introducing the electrode system includes introducing an expandable anchor having a flexible insulative substrate thereon, and at least one electrode on the substrate.

9. The method of claim 8, wherein introducing the electrode system includes introducing an expandable anchor having a silicone insulative substrate thereon, and at least one electrode on the silicone substrate.

* * * * *